(12) United States Patent
Katekari

(10) Patent No.: US 11,741,600 B2
(45) Date of Patent: Aug. 29, 2023

(54) IDENTIFYING FOLLICULAR UNITS

(71) Applicant: Santosh Sharad Katekari, Orlando, FL (US)

(72) Inventor: Santosh Sharad Katekari, Orlando, FL (US)

( * ) Notice: Subject to any disclaimer, the term of this patent is extended or adjusted under 35 U.S.C. 154(b) by 373 days.

(21) Appl. No.: 17/237,014

(22) Filed: Apr. 21, 2021

(65) Prior Publication Data

US 2022/0343493 A1 Oct. 27, 2022

(51) Int. Cl.
*G06T 7/00* (2017.01)
*G02B 27/01* (2006.01)
*A61B 34/37* (2016.01)
*A61B 90/00* (2016.01)

(52) U.S. Cl.
CPC ............ *G06T 7/0012* (2013.01); *A61B 34/37* (2016.02); *A61B 90/36* (2016.02); *G02B 27/017* (2013.01); *A61B 2090/365* (2016.02); *G02B 2027/0178* (2013.01); *G06T 2207/10028* (2013.01); *G06T 2207/20021* (2013.01); *G06T 2207/20081* (2013.01); *G06T 2207/30004* (2013.01)

(58) Field of Classification Search
CPC ......... G06T 7/0012; G06T 2207/10028; G06T 2207/20021; G06T 2207/20081; G06T 2207/30004; G06T 2207/30088; G06T 2207/30242; A61B 34/37; A61B 90/36; A61B 2090/365; A61B 2017/00752; A61B 2034/105; A61B 34/25; A61B 34/30; A61B 2034/2065; A61B 2090/367; A61B 2090/372; A61B 2090/502; G02B 27/017; G02B 2027/0178; G02B 27/01
See application file for complete search history.

(56) References Cited

U.S. PATENT DOCUMENTS

| 8,290,229 | B2 | 10/2012 | Qureshi et al. |
| 9,107,697 | B2 | 8/2015 | Qureshi et al. |
| 9,576,359 | B2 | 2/2017 | Rahman et al. |
| 10,327,850 | B2 | 6/2019 | Bodduluri et al. |
| 2016/0253799 | A1* | 9/2016 | Rahman ................ G06T 7/0012 382/128 |
| 2018/0080865 | A1* | 3/2018 | Godfrey .................. G06F 18/22 |
| 2020/0000964 | A1* | 1/2020 | Kim .................... A61L 27/3691 |

* cited by examiner

*Primary Examiner* — Siamak Harandi
(74) *Attorney, Agent, or Firm* — KAPatents

(57) ABSTRACT

A follicular unit harvesting process receives images for analysis and identifies and highlights clusters of hair. The analysis includes pixel type determination, pixel clustering, cluster classification and cluster highlighting or replacement. The analysis of the pixels is performed concurrently, and the results of the analysis are optionally used for automated treatment planning.

20 Claims, 13 Drawing Sheets

IDENTIFYING FOLLICULAR UNITS

TECHNICAL FIELD

The present invention relates generally to a method, system, and computer program product, for identifying follicular units(grafts) on an area of a body surface such as a scalp during a hair transplant procedure. More particularly, the present invention relates to a method, system, and computer program product for the examination of the scalp to identify, classify and localize follicular units in the donor area for hair harvesting.

BACKGROUND

Presently, technology exists to extract hair from a part of a body surface (e.g. a back portion of the scalp) having abundant hair to another part of the body surface (e.g. a front, balding portion of the scalp). For example, after cleaning the scalp, a surgeon uses a small needle to numb an area of the head using local anesthesia and extracts and implants skin or hair follicles from the back portion to the balding portion. In a follicular unit extraction process, hair follicles are cut out directly from the back of the scalp through a plurality of minute punch incisions with the surgeon making tiny holes with a blade or needle in the scalp that receives the cut-out hair follicles. The cut-out hair follicles are then carefully placed in the tiny holes created in the balding portion. An extraction and implantation session can take multiple hours to complete, and the accuracy of appropriate patient-specific follicles that are identified for extraction and implantation varies from surgeon to surgeon.

SUMMARY

The illustrative embodiments provide a method, system, and computer program product. In an aspect herein, a computer-implemented method is disclosed. The computer-implemented method includes: a) receiving a first image of a body surface having a plurality of hair follicles for harvesting; b) classifying pixels of the image into hair pixels and non-hair pixels types, based on a partitioning of category values of said hair pixels from category values of said non-hair pixels, the category values being representative of statistical properties of the hair and non-hair pixels; c) grouping, responsive to the classifying, a collection of proximal classified hair pixels together to form a cluster of hair pixels that is indicative of a follicular unit; and d) categorizing the follicular unit, responsive to the grouping and based on area parameters of pixels related to the cluster of hair pixels, into a type that is indicative of the number of hair follicles in the follicular unit.

In another aspect, the method includes receiving one or more other images in a live sequence and repeating steps a)-d) for the one or more other images. Further, the categorized/codified follicular unit may be highlighted by replacing pixels of said codified follicular unit in the image with pixels that indicate one or more visual cues, such as color, which correspond to the type that is codified for the follicular unit. The one or more visual cues are visual cues selected from the group consisting of colors, numbers, shapes and textures. The method may also include projecting the live sequence on an augmented reality (AR) glasses or heads up display (HUD). The grouping of the collection of proximal classified hair pixels can be based on a flood fill algorithm and the area parameters may include an area of the subject follicular unit under consideration area (FUA-d), which is a count of all the hair pixels in a subject follicular unit under consideration., a maximum area for a 1-hair-follicular unit (1-FUA-c) in FUA-d, and a dynamic axis aligned bounding area (BA-d), and ratios thereof. In a further aspect, the classifying step of the method is performed in a parallel manner and is achieved by dividing the first image into sub-images, each sub-image comprising at least one pixel and classifying one of the sub images concurrently as at least another of the sub-images is classified, using a graphics processing unit (GPU) in order to increase a speed of classification in comparison to conventional serial classifications. The grouping can be performed in a parallel manner using said sub-images and the GPU. In another step, an area of the body surface is imaged in a donor scan process in order to obtain a 3D point cloud or 3D model of the body surface. The method may also include calculating a number and the type of follicular units to harvest form the body surface based on any combination of (i) a determined grade of baldness, (ii) a determined number of different types of follicular units on the body surface, (iii) a desired final look and (iv) a defined set of harvesting/implantation rules. The method further includes detecting a movement of an operator's handpiece on the body surface and moving a robotic arm having a camera to follow the movement in order to automatically capture a live video of the body surface proximal to the operator's handpiece. A textual report may be displayed that includes information about the codified follicular unit and updating the report dynamically based on the one or more other images.

In another aspect herein, a system is disclosed. The system includes at least one processor configured to perform the steps comprising: a) receiving a first image of a body surface having a plurality of hair follicles for harvesting; b) classifying pixels of the image into hair pixels and non-hair pixels types, based on a partitioning of category values of said hair pixels from category values of said non-hair pixels, the category values being representative of statistical properties of the hair and non-hair pixels; c) grouping, responsive to the classifying, a collection of proximal classified hair pixels together to form a cluster of hair pixels that is indicative of a follicular unit; and d) codifying the follicular unit, responsive to the grouping and based on area parameters of pixels related to the cluster of hair pixels, into a type that is indicative of the number of hair follicles in the follicular unit.

In yet another aster, a non-transitory computer-readable storage medium is disclosed. The non-transitory computer-readable storage medium stores a program which, when executed by a processor, causes the processor to perform a procedure comprising: a) receiving a first image of a body surface having a plurality of hair follicles for harvesting; b) classifying pixels of the image into hair pixels and non-hair pixels types, based on a partitioning of category values of said hair pixels from category values of said non-hair pixels, the category values being representative of statistical properties of the hair and non-hair pixels; c) grouping, responsive to the classifying, a collection of proximal classified hair pixels together to form a cluster of hair pixels that is indicative of a follicular unit; and d) codifying the follicular unit, responsive to the grouping and based on area parameters of pixels related to the cluster of hair pixels, into a type that is indicative of the number of hair follicles in the follicular unit.

An embodiment includes a computer usable program product. The computer usable program product includes a computer-readable storage device, and program instructions stored on the storage device.

An embodiment includes a computer system. The computer system includes a processor, a computer-readable memory, and a computer-readable storage device, and program instructions stored on the storage device for execution by the processor via the memory.

BRIEF DESCRIPTION OF THE DRAWINGS

Certain novel features believed characteristic of the invention are set forth in the appended claims. The invention itself, however, as well as a preferred mode of use, further objectives, and advantages thereof, will best be understood by reference to the following detailed description of the illustrative embodiments when read in conjunction with the accompanying drawings, wherein:

DETAILED DESCRIPTION

Figure 1:
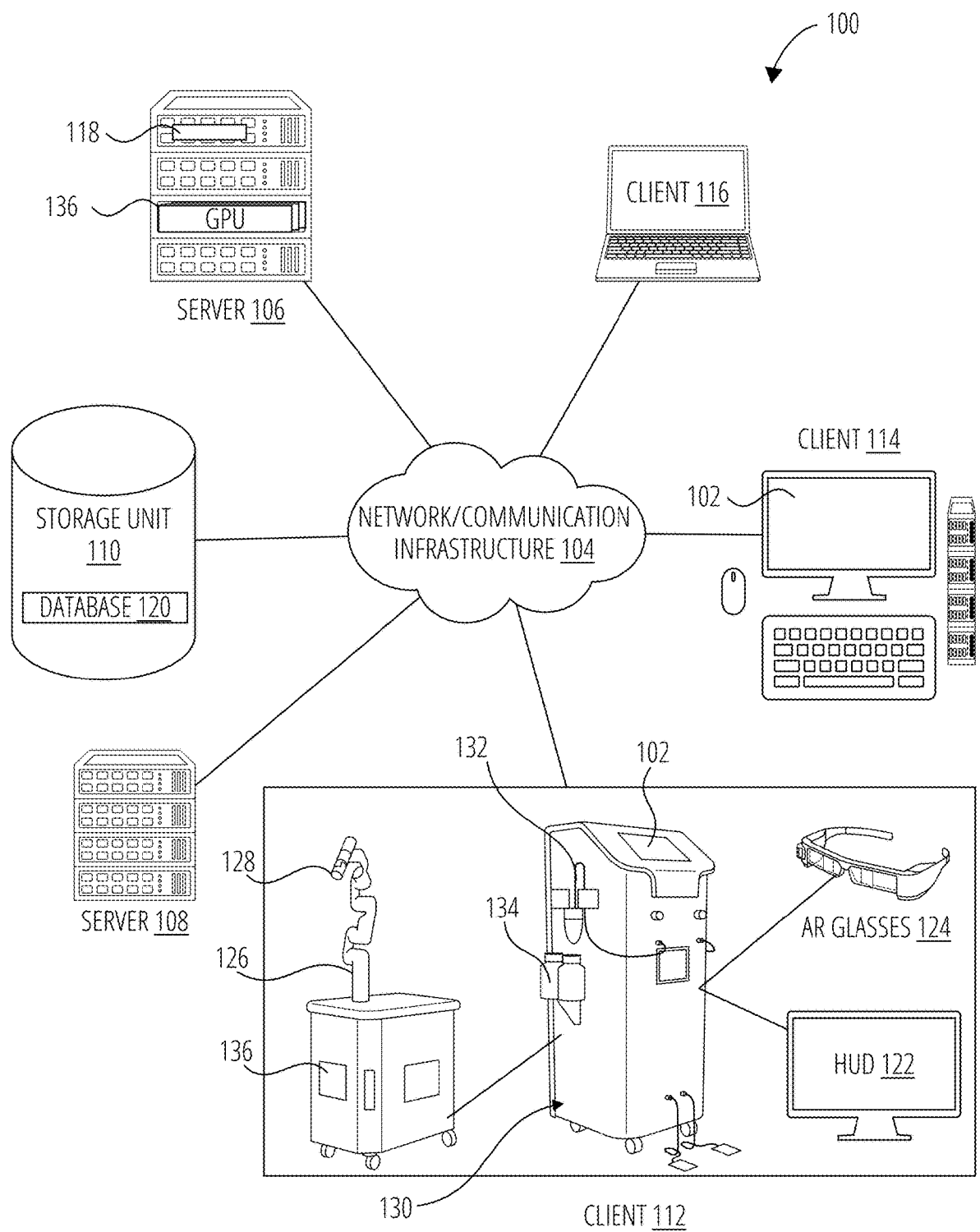
FIG. 1 depicts a block diagram of a network of data processing systems in which illustrative embodiments may be implemented.

The illustrative embodiments recognize that hair harvesting procedures requires incredible precision, dexterity, skills in identifying correct hair follicles and follicular units to harvest and implanting them to optimize a patient specific outcome. Even experienced surgeons working with currently available technology find it difficult to create a treatment plan and execution that takes into consideration the particular follicular units available on a patient-specific body surface and how harvesting of these units affects the overall outcome of the treatment. The illustrative embodiments further recognize that in some existing harvesting processes, images of a body surface to be treated (e.g., a scalp) are taken and pixels belonging to hair are differentiated from pixels belonging to skin by mapping each pixel to a defined range of color values corresponding to hair or skin. However, the ranges may vary from person to person and a range indicative of hair pixels for one individual may not be indicative of hair pixels for another individual.

The illustrative embodiments further recognize that while hair harvesting can be presently achieved by surgeons with the aid of robotic arms and images, the methods are crude and limited in utility. For example, as far as the viewing of follicular units, surgeons acquire single images of the body surface, usually one at a time, for manual analysis of hairs and follicular hair units, thus requiring a large amount of time in a planning phase due to the manual nature. Further, there is a need to use markers to identify a donor area and keep the patient's head stationary during conventional extraction procedures such that any head movements cause positioning problems for a robotic arm. Moreover, a surgeon's/user's/operator's attention to identified follicular hair units is not a fixed entity. By providing, based on accurate identification and classification of follicular units in images, optimized viewing solutions such as, an ability to detect follicular units in real time by visual cues even with patient and operator movements, an ability to follow the operator's point of view/perspective or handpiece movements automatically, an availability of magnified field of view, an availability of high resolution images/video, and/or otherwise an ability to provide a variety of factors that influence accuracy of harvesting, an optimized harvesting and implantation system may be achieved. For example, even if an operator can visually analyze a given image or enhanced/annotated images, several distinct other images of a patient's body surface have to be taken and analyzed to create a treatment plan. The present state of the technological field of endeavor of hair harvesting presently does not include apparatus to provide optimized illustrations and identification of follicular hair units in real time based on computed properties of hair. By providing such solutions that solve a need exists for optimized patient-specific guidance of the process of hair harvesting in a manner as described herein, the overall outcome of a treatment implementation is improved.

The illustrative embodiments recognize that the presently available tools or solutions do not address these needs/problems or provide adequate solutions for these needs/problems. The illustrative embodiments used to describe the invention generally address and solve the above-described problems and other related problems by optimized identification and classification of follicular units.

An embodiment provides cues (such as visual cues) about determined properties of follicular hair units available in a given area in real time for a decision-making process of the operator. An embodiment provides information about identified follicular units for a decision-making process of a robotic arms. Even further, an embodiment provides information about follicular hair units for use by other devices and process discussed herein.

An embodiment provides an analysis of a patient's donor area through defined color codes that correspond to respective follicular units. The embodiment further provides information about a count of follicular units in a defined area/donor area (e.g., 85 total follicular units in a defined area of the scalp). The embodiment further provides information about a type of follicular unit in the defined area (e.g.

twenty-six total follicular units in the defined area each having 4 hair follicles, i.e. twenty-six total 4-hair follicular units). The embodiment also provides information about a number of follicular units that exceed a defined threshold (e.g. seven follicular units that each comprise at least 5 hair follicles, i.e. seven 5 or more hair-follicular units). The embodiment also provides information about a number of different types of follicular units that are present in a defined area.

Another embodiment displays the analysis as visual color codes superimposed on a real-time video/real-time image sequence of the patient. The real-time video and the visual color codes may be displayed on a display unit, an integrated heads-up-display (HUD) and/or an integrated augmented-reality (AR) glasses. For example, in the AR glasses, by projecting the real-time video and superimposed visual color codes, that are superimposed on corresponding follicular units, in a field of view of the operator, a real-time tracking of the donor area can be achieved. Of course, other ways of identifying follicular units without the use of visual color codes, such as visual patterns/shapes, numerical identifications or textures are possible in light of the specification. Further, the defined area of interest changes in real-time based on a position of a camera of the robotic arm which tracks an area of interest, and the embodiment updates the superimposed analysis based on said current area of interest. For example, the area of interest is based on and follows a position of the operator's handpiece on the scalp or tool tip of a display, thus by the movement of the operator's handpiece along the body surface of the patient or tool tip along the display, the superimposed real-time analysis is updated to indicate an analysis that corresponds to the an area of interest proximal to the operator's handpiece. In another example, the area of interest focused on by the camera of the robotic arm is based on a defined extraction strategy or sequence, wherein, for example, all twenty six 4-hair follicular units are harvested one after the other in a guided manner by a processor operating the robotic arm to navigate the twenty six 4-hair follicular units in succession based on their identified locations or other available property. In another example, the update or hair analysis and corresponding visual cue projection is done for every newly obtained image in a live video sequence. In another example, the update is a defined number of times in a given time frame. The embodiment may also display the analysis in a textual form. Further, the embodiment may compute an analysis on a fixed area of interest marked or determined by the operator.

Another embodiment achieves significantly high resolution (e.g. 2K-4K resolution or more) in comparison with conventional solutions by using graphics processing units (GPUs). The GPUs rapidly manipulate and alter memory to accelerate the creation of images in a frame buffer intended for output to a display device in real time. The parallel structure of GPUs allows the processing of large blocks of data in parallel. Thus, by dividing a high resolution captured image into a plurality of sections for follicular hair unit for identification in those respective sections, in a parallel rather than serial manner, a significantly faster performance with higher resolution is achieved in comparison with conventional methods. In this example, each section represents one pixel and the parallel computations may be achieved with a GPU. In another example each image is divided into section representing a plurality of proximal pixels with computations on each section being conducted in a parallel fashion.

An embodiment provides a magnification (e.g. 40-60 times, 50 times) of a donor area. The robotic arm scans or takes a plurality of images that encompass the donor area based on a defined starting and ending point to obtain a 3D point cloud and produces a follicular unit analysis or static report of the scanned area. Further, an application is configured to estimate a total number of follicular units required for a specific patient based on the patient's degree of baldness. The application further computes, using the scan, a number of follicular units and of what type should be extracted and implanted in different areas of the scalp.

The manner of optimized identification and classification of follicular units described herein is unavailable in the presently available methods in the technological field of endeavor pertaining to hair harvesting. A method of an embodiment described herein, when implemented to execute on a device or data processing system, comprises substantial advancement of the functionality of that device or data processing system in hair harvesting by accurately identifying different types of follicular units and visualizing them in real time for harvesting.

The illustrative embodiments are described with respect to certain types of data, functions, algorithms, equations, model configurations, locations of embodiments, additional data, devices, data processing systems, environments, components, and applications only as examples. Any specific manifestations of these and other similar artifacts are not intended to be limiting to the invention. Any suitable manifestation of these and other similar artifacts can be selected within the scope of the illustrative embodiments.

Furthermore, the illustrative embodiments may be implemented with respect to any type of data, data source, or access to a data source over a data network. Any type of data storage device may provide the data to an embodiment of the invention, either locally at a data processing system or over a data network, within the scope of the invention.

The illustrative embodiments are described using specific code, designs, architectures, protocols, layouts, schematics, and tools only as examples and are not limiting to the illustrative embodiments. Furthermore, the illustrative embodiments are described in some instances using particular software, tools, and data processing environments only as an example for the clarity of the description. The illustrative embodiments may be used in conjunction with other comparable or similarly purposed structures, systems, applications, or architectures. For example, other comparable mobile devices, structures, systems, applications, or architectures therefor, may be used in conjunction with such embodiment of the invention within the scope of the invention. An illustrative embodiment may be implemented in hardware, software, or a combination thereof.

The examples in this disclosure are used only for the clarity of the description and are not limiting to the illustrative embodiments. Additional data, operations, actions, tasks, activities, and manipulations will be conceivable from this disclosure and the same are contemplated within the scope of the illustrative embodiments.

Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above.

Figure 2:
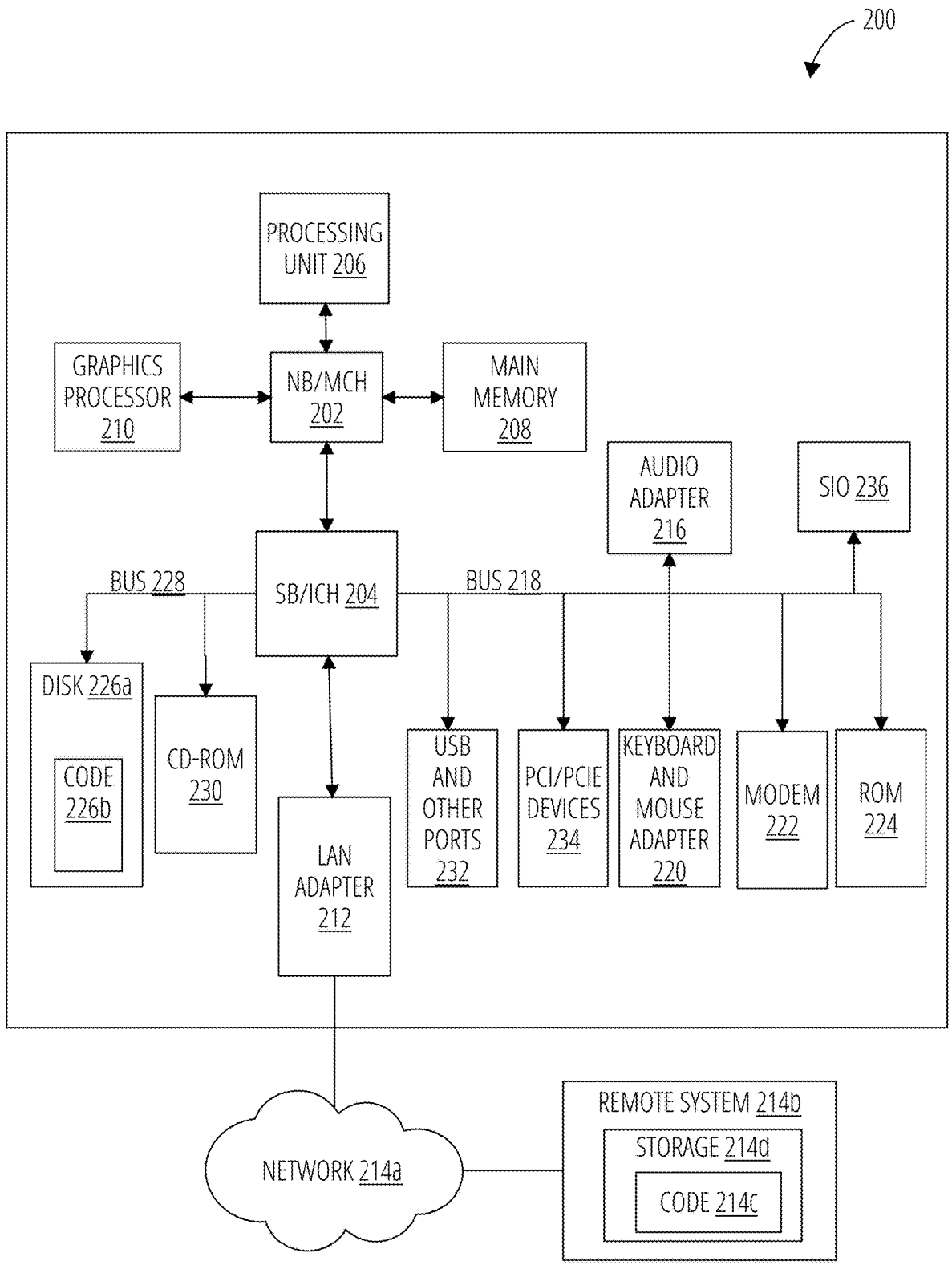
FIG. 2 depicts a block diagram of a data processing system in which illustrative embodiments may be implemented.

With reference to the figures and in particular with reference to FIGS. 1 and 2, these figures are example diagrams of data processing environments in which illustrative embodiments may be implemented. FIGS. 1 and 2 are only examples and are not intended to assert or imply any limitation with regard to the environments in which different embodiments may be implemented. A particular implementation may make many modifications to the depicted environments based on the following description.

With reference to the figures and in particular with reference to FIG. 1 and FIG. 2, these figures are example diagrams of data processing environments in which illustrative embodiments may be implemented. FIG. 1 and FIG. 2 are only examples and are not intended to assert or imply any limitation with regard to the environments in which different embodiments may be implemented. A particular implementation may make many modifications to the depicted environments based on the following description.

FIG. 1 depicts a block diagram of a network of data processing systems in which illustrative embodiments may be implemented. Data processing environment is a network of computers in which the illustrative embodiments may be implemented. Data processing environment 100 includes network/communication infrastructure 104. Network/communication infrastructure 104 is the medium used to provide communications links between various devices, databases and computers connected together within data processing environment 100. Network/communication infrastructure 104 may include connections, such as wire, wireless communication links, or fiber optic cables.

Clients or servers are only example roles of certain data processing systems connected to network/communication infrastructure 104 and are not intended to exclude other configurations or roles for these data processing systems. Server 106 and server 108 couple to network/communication infrastructure 104 along with storage unit 110 which includes a database 120 for storage of data such as images. Software applications may execute on any computer in data processing environment 100. Client 112, client 114, client 116 are also coupled to network/communication infrastructure 104. Client 112 may be a hair harvesting and implantation system having an extraction unit 130 with a display for operator/user input. The extraction unit 130 may also have an application 102 and may be operatively coupled to a display such as a heads-up-display (HUD 122) or an augmented reality AR Glasses 124. It may also be operatively coupled to a robotic arm 126 having a camera 128, and extraction handpiece 132 and a storage jar 134. The robotic arm 126 includes one or more sensors in a camera 128 that measure a surface by obtaining a plurality of images through projections that for a live video view of a body surface.

A data processing system, such as server 106 or server 108, or clients (client 112, client 114, client 116) may contain data and may have software applications or software tools executing thereon.

Only as an example, and without implying any limitation to such architecture, FIG. 1 depicts certain components that are usable in an example implementation of an embodiment. For example, servers and clients are only examples and do not to imply a limitation to a client-server architecture. As another example, an embodiment can be distributed across several data processing systems and a data network as shown, whereas another embodiment can be implemented on a single data processing system within the scope of the illustrative embodiments. Data processing systems (server 106, server 108, client 112, client 114, client 116) also represent example nodes in a cluster, partitions, and other configurations suitable for implementing an embodiment.

Application 102 which may reside on a client 114 or extraction unit 130 or any other application such as server application 118 implements an embodiment described herein. Any of the clients or servers or portions thereof may include one or more GPUs 136 by which analysis of follicular units contained in images may be conducted. In an example, the images are each divided into a plurality of sub-images to determine properties about follicular hair units present in said sub-images in order to obtain fast processing and analyses times in comparison to conventional solutions. In the example, each sub-image may comprise one pixel. Storage unit 110 may store information about the analysis. Application 102 can obtain single frame images such as 2D images from the camera 128 and analyze follicular units using said single frame images. Application 102 can also obtain data from storage unit 110 for rendering or characterization. Further, client application projects analyses of follicular hair units using an image sequence/video of the patient and projects them for viewing using AR Glasses 124 and/or HUD 122 such that the analyses appear superimposed on the patient's body surface in the video. Application 102 can also execute in any of data processing systems (server 106 or server 108, client 112, client 114, client 116), such as client application 118 in server 106 and need not execute in the same system as client 112.

Server 106, server 108, storage unit 110, client 112, client 114, client 116, may couple to network/communication infrastructure 104 using wired connections, wireless communication protocols, or other suitable data connectivity. Client 112, client 114 and client 116 may be, for example, personal computers or network computers.

In the depicted example, server 106 may provide data, such as boot files, operating system images, and applications to client 112, client 114, and client 116. Client 112, client 114 and client 116 may be clients to server 106 in this example. Client 112, client 114 and client 116 or some combination thereof, may include their own data, boot files, operating system images, and applications. Data processing environment 100 may include additional servers, clients, and other devices that are not shown. Server 106 includes an application 118 that may be configured to implement one or more of the functions described herein for displaying a live control view in accordance with one or more embodiments.

Server 108 may include a search engine configured to search stored files such as images of patients in response to a request from the operator with respect to various embodiments.

In the depicted example, data processing environment 100 may be the Internet. Network/communication infrastructure 104 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a client data processing system and a server data processing system. Data processing environment 100 may also employ a service-oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a computer, such client 112, client 114, client 116 or s server 106, server 108, in FIG. 1, or another type of device in which computer usable program code or instructions implementing the processes may be located for the illustrative embodiments.

Data processing system 200 is described as a computer only as an example, without being limited thereto. Implementations in the form of other devices, in FIG. 1, may modify data processing system 200, such as by adding a touch interface, and even eliminate certain depicted components from data processing system 200 without departing from the general description of the operations and functions of data processing system 200 described herein.

In the depicted example, data processing system 200 employs a hub architecture including North Bridge and memory controller hub (NB/MCH) 202 and South Bridge and input/output (I/O) controller hub (SB/ICH) 204. Processing unit 206, main memory 208, and graphics processor 210 are coupled to North Bridge and memory controller hub (NB/MCH) 202. Processing unit 206 may contain one or more processors and may be implemented using one or more heterogeneous processor systems. Processing unit 206 may be a multi-core processor. Graphics processor 210 may be coupled to North Bridge and memory controller hub (NB/MCH) 202 through an accelerated graphics port (AGP) in certain implementations.

In the depicted example, local area network (LAN) adapter 212 is coupled to South Bridge and input/output (I/O) controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and input/output (I/O) controller hub (SB/ICH) 204 through bus 218. Hard disk drive (HDD) or solid-state drive (SSD) 226a and CD-ROM 230 are coupled to South Bridge and input/output (I/O) controller hub (SB/ICH) 204 through bus 228. PCI/PCIe devices 234 may include, for example, Ethernet adapters, add-in cards, and PC cards for notebook computers. PCI uses a card bus controller, while PCIe does not. Read only memory (ROM) 224 may be, for example, a flash binary input/output system (BIOS). Hard disk drive (HDD) or solid-state drive (SSD) 226a and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and input/output (I/O) controller hub (SB/ICH) 204 through bus 218.

Memories, such as main memory 208, read only memory (ROM) 224, or flash memory (not shown), are some examples of computer usable storage devices. Hard disk drive (HDD) or solid-state drive (SSD) 226a, CD-ROM 230, and other similarly usable devices are some examples of computer usable storage devices including a computer usable storage medium.

An operating system runs on processing unit 206. The operating system coordinates and provides control of various components within data processing system 200 in FIG. 2. The operating system may be a commercially available operating system for any type of computing platform, including but not limited to server systems, personal computers, and mobile devices. An object oriented or other type of programming system may operate in conjunction with the operating system and provide calls to the operating system from programs or applications executing on data processing system 200.

Instructions for the operating system, the object-oriented programming system, and applications or programs, such as application 118 and application 102 in FIG. 1, are located on storage devices, such as in the form of codes 226b on Hard disk drive (HDD) or solid-state drive (SSD) 226a, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory (ROM) 224, or in one or more peripheral devices.

Furthermore, in one case, code 226b may be downloaded over network 214a from remote system 214b, where similar code 214c is stored on a storage device 214d in another case, code 226b may be downloaded over network 214a to remote system 214b, where downloaded code 214c is stored on a storage device 214d.

The hardware in FIG. 1 and FIG. 2 may vary depending on the implementation. Other internal hardware or peripheral devices, such as flash memory, equivalent non-volatile memory, or optical disk drives and the like, may be used in addition to or in place of the hardware depicted in FIG. 1 and FIG. 2. In addition, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may comprise one or more buses, such as a system bus, an I/O bus, and a PCI bus. Of course, the bus system may be implemented using any type of communications fabric or architecture that provides for a transfer of data between different components or devices attached to the fabric or architecture.

A communications unit may include one or more devices used to transmit and receive data, such as a modem or a network adapter. A memory may be, for example, main memory 208 or a cache, such as the cache found in North Bridge and memory controller hub (NB/MCH) 202. A processing unit may include one or more processors or CPUs.

The depicted examples in FIG. 1 and FIG. 2 and above-described examples are not meant to imply architectural limitations. For example, data processing system 200 also may be a tablet computer, laptop computer, or telephone device in addition to taking the form of a mobile or wearable device.

Where a computer or data processing system is described as a virtual machine, a virtual device, or a virtual component, the virtual machine, virtual device, or the virtual component operates in the manner of data processing system 200 using virtualized manifestation of some or all components depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and Hard disk drive (HDD) or solid-state drive (SSD) 226a is manifested as a virtualized instance of all or some portion of Hard disk drive (HDD) or solid-state drive (SSD) 226a that may be available in the host data processing system. The host data processing system in such cases is represented by data processing system 200.

Figure 3A:
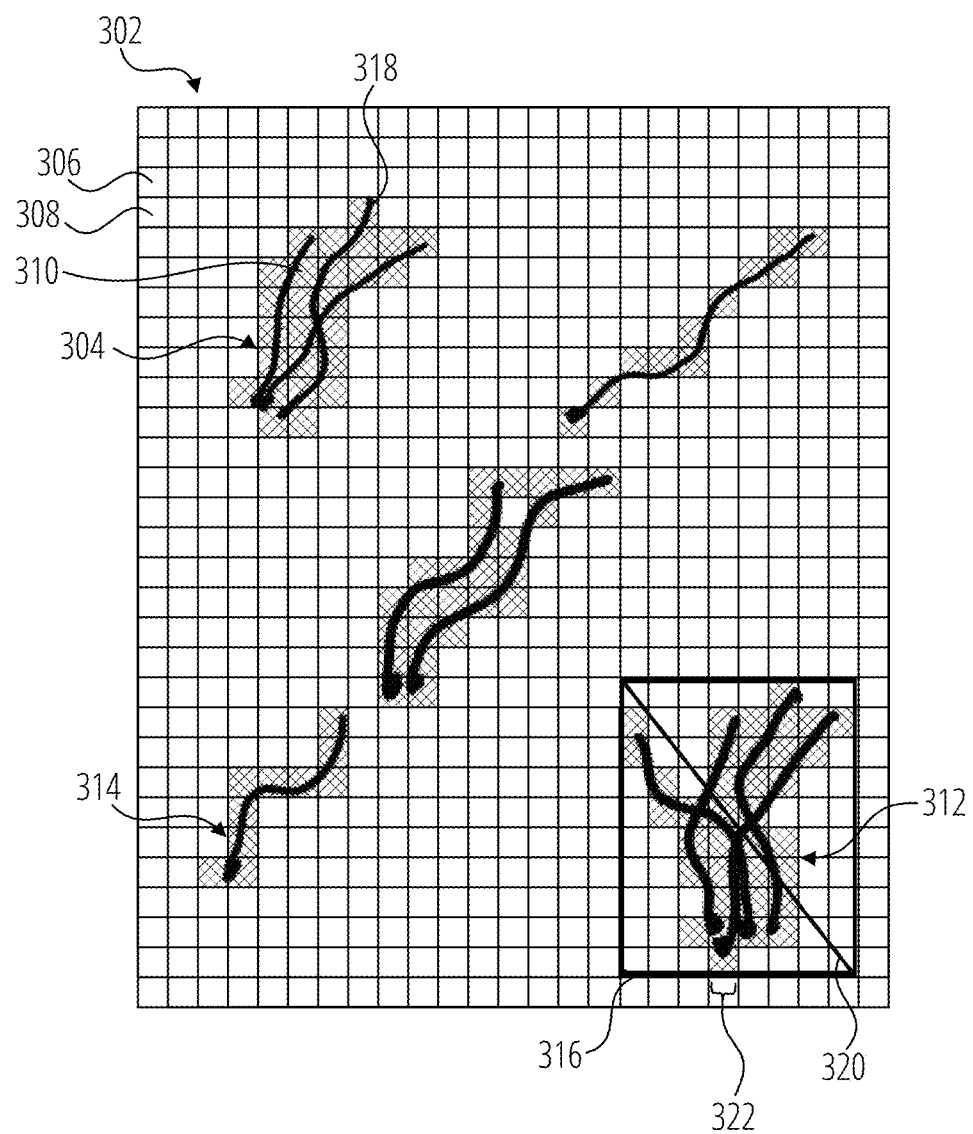
FIG. 3A depicts a sketch of an image in accordance with an illustrative embodiment.

With reference to FIG. 3A, this figure depicts an image 302 having pixels 306 representative of hair follicles (hair pixels 310, which are shaded for illustration) and pixels representative of the absence of hair (non-hair pixels 308, such as pixels representative of skin). Hair 318 is shown as being superimposed on the hair pixels 310 in FIG. 3A simply for illustration purposes. The presence or absence of hair is determined by a classification of the pixel based on its color in a computation that works for different types of hair from different individuals as described hereinafter. The image also shows collections of hair follicles that form a follicular unit 304 such as a 4-hair follicular unit 312 or a 1-hair follicular unit 314.

Figure 4:
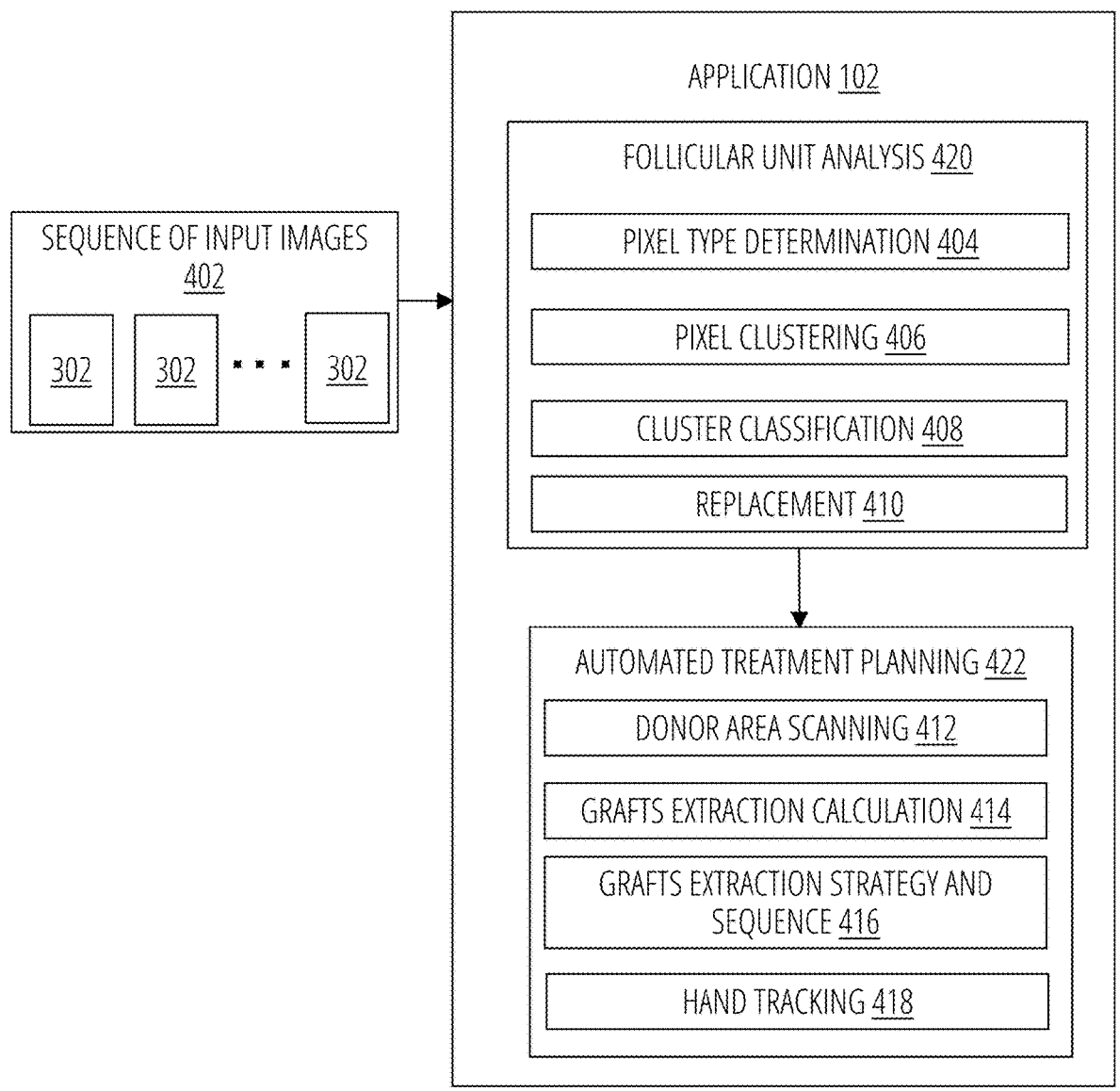
FIG. 4 depicts a block diagram of an example configuration for optimized identification and classification of follicular units in accordance with an illustrative embodiment.

With reference to FIG. 4, this figure depicts a block diagram of an example configuration for identifying and classifying follicular units for automated treatment planning in accordance with an illustrative embodiment. Application 102 is an example of any of applications 118 and 102 in FIG. 1, depending upon the particular implementation.

Application 102 receives a temporal sequence of input images 402 for follicular unit analysis 420. Each image 302 in the sequence is analyzed to more accurately, identify and classify follicular units, compared to conventional processes, which are then highlighted by visual cues for treatment planning and execution. The analysis includes a pixel type determination 404, a pixel clustering 406, a cluster classification 408 and a display of visual cues, in a replacement 410 step, on identified follicular units. However, the illustrative embodiments recognize that high resolution images may contain millions of pixels 306 and thus computations involving pixels, if conducted in a serial fashion, will slow down a hair harvesting system such as client 112. A GPU 136 is therefore employed to accelerate application 102 by offloading the analyses of the pixels 306. A CPU includes, for example four to ten CPU cores, while the GPU 136 includes hundreds or thousands of smaller cores. Together, they operate to analyze properties of pixels 306 in the application 102. This massively parallel architecture gives the GPU 136 its high compute performance and allows the real-time identification and classification of follicular units even with patient and operator movements as discussed herein. A GPU includes a large number of vector math based CPUs that could process in magnitude of 1000 instructions simultaneously. An image comprises pixel elements where each pixel or some group of them needs to be processed. GPU becomes a natural choice to process these pixels or group of pixels simultaneously in one frame of computation to achieve real-time performance. Each pixel or group of pixel is mapped to one CPU of the GPU, for example, some or all algorithms and computations described herein are achieved in an accelerated manner. For a 4K image on a moderately high-end GPU the FPS (frames per second) after image processing algorithms may reach up to 20 FPS while using CPU based data transferring of images between CPU to GPU. The illustrative embodiments further recognize that simply mapping color values of pixels to a predefined range that supposedly indicates the presence of hair, as is common in conventional systems, produces inaccurate results as one range that indicates hair for one individual may not indicate hair for another individual. Thus, a more accurate categorization of hair and non-hair pixels that works for variable input images from different individuals is needed.

Figure 5A:
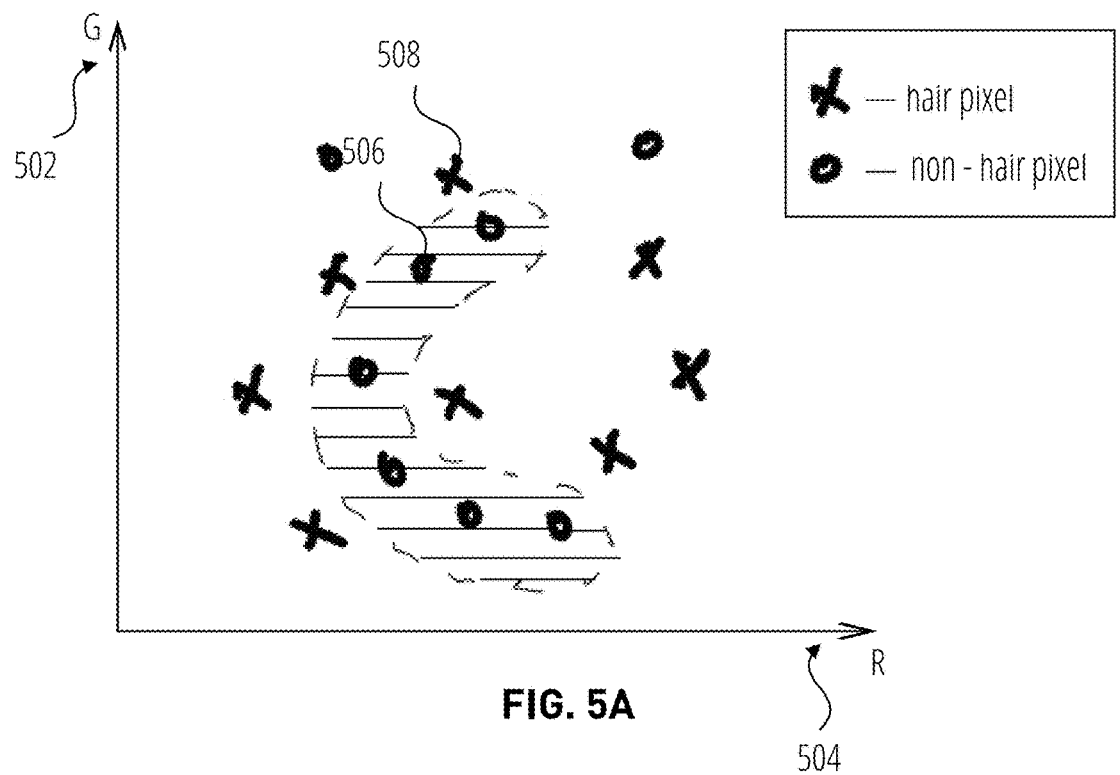
FIG. 5A depicts a chart in accordance with an illustrative embodiment.
Figure 5B:
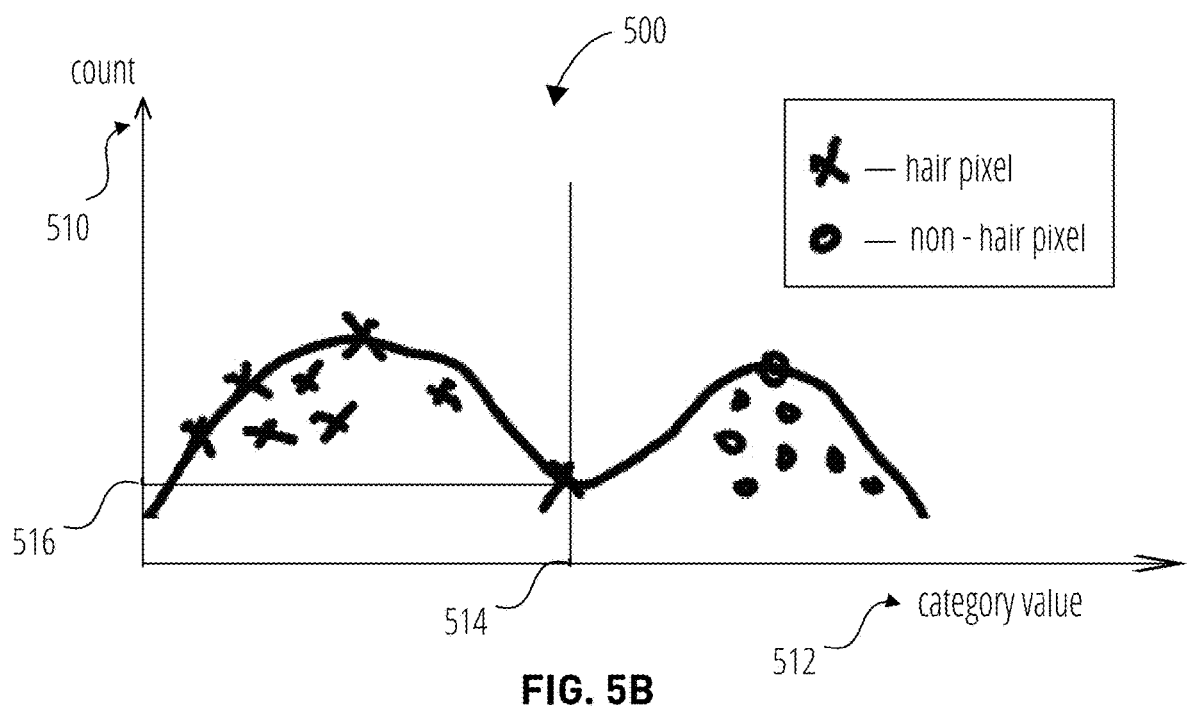
FIG. 5B depicts another chart in accordance with an illustrative embodiment.

The pixel type determination 404 begins by the receipt of an image 302. The image is divided into sub-images for computations by the GPU 136, each sub-image including at least one pixel. In an illustrative embodiment, calculations by the GPU 136 are done for each pixel of the image 302. The pixels 306 of the image 302 are analyzed in parallel by the GPU 136 to classify them as hair or non-hair (e.g. Skin) pixels. This is achieved as follows. Each pixel 306 has an r, g, b value as shown in FIG. 5A using only r, red color value 504 and g, green color value 502 for simplicity. The chart shows a plot of color values for hair pixels 508 against color values for non-hair pixels 506. Though a pattern appears for the plotted color values for non-hair pixels 506, it is not trivial to computationally differentiate values representing hair pixels from values representing non-hair pixels. In order to achieve said differentiation, a category value partitioning process is performed. This begins with an integer division step that is carried out on the r, g, b values in order to obtain ri, gi, bi, where ri, gi, bi, allow integer representations of color values to be obtained for use in determining category values 512 for a histogram 500 that partitions factors associated with hair pixels from factors associated with non-hair pixels. A category value 512 of the pixel is obtained, the category value 512 being configured to push "factors" of non-hair/skin pixels 308 to one side of a histogram and "factors" of hair pixels 310 to another side of the histogram for separation/differentiation as shown in FIG. 5B. In FIG. 5B, the histogram 500 shows a count 510 of computed category values 512. Pixels are classified as hair pixels 310 or non-hair pixels 308 by determining a first local minima 516 of the category values 512 and setting the corresponding category value as a threshold category value 514. Therefore any pixel 306 having a category value 512 that is less than the threshold category value 514 can be classified or codified as a hair pixel 310 and any pixel having a category value 512 higher than the threshold category value 514 can be classified as a non-hair pixel 308.

Obtain Category Value of Pixel for Histogram a) input (r, g, b)
b) ri=255/r, gi=255/g, bi=255/bi–Perform integer division
c) category value=10^3/(ri*gi*bi)

Classify Pixel into Hair or Skin using Histogram a) for all category values of all the pixels in the image, compute histogram
b) compute first local minima in histogram and let it be threshold
c) for any pixel if the category value<threshold then it is a hair pixel After classifying the pixels 306 into hair and non-hair pixels pixel types, the pixels are clustered in a pixel clustering 406 step. In an embodiment, this is achieved using the parallel architecture of the GPU 136 in order to provide fast clustering. Based on the pixel type classifications obtained from the pixel type determination 404 steps, a collection of proximal pixels that have been classified as hair pixels 310 are grouped together to form a cluster of hair pixels indicative of a graft of hair. This is achieved by, for example, polygon filling algorithms such as the flood fill algorithm wherein pixels connected to a given pixel that match a given attribute are identified and grouped together to form a cluster. Herein the given attribute is the pixel type of a connected pixel being a hair pixel 310 as dictated by the pixel type determination 404. In an illustrative embodiment, a start pixel, a target color and a replacement color are obtained as parameters. Pixels that are directly connected to a start hair pixel, or indirectly through a continuous path of one or more other hair pixels are identified based on their pixel type/target color by the flood fill algorithm. This may be achieved in a parallel fashion using the GPU 136. In the embodiment, the hair pixels are classified as part of a cluster or graft of hair and may be subsequently replaced by a replacement color or visual cue that helps to visually identify/differentiate the cluster or graft of hair from other clusters/other grafts hair and skin as discussed herein.

In a next step, a cluster classification 408 is performed wherein different clusters are classified into types of follicular units indicative of the number of hair follicles in the cluster/graft of hair. Assuming one hair pixel width is constant for an individual, the cluster classification 408 is done based on parameters of pixels related to a follicular unit including the count of all the hair pixels in a subject follicular units under consideration (FUA-d), a maximum area for a 1-hair-follicular unit (1-FUA-c) in a FUA-d, an axis aligned bounding area 316 (BA-d), a length (L) of a diagonal 320 of the axis aligned bounding area and ratios thereof, wherein the area of the follicular unit under consideration(FUA-d) represents an area in the image 302 covered by all hair pixels of a subject follicular unit/follicular unit under consideration (e.g. an area of 36 pixels for the example 4-hair follicular unit 312), wherein the area for a 1-hair-follicular unit (1-FUA-c) represents the maximum area covered by equivalent pixels of one hair follicle in the follicular unit under consideration, wherein the axis aligned bounding area 316 (BA-d) represents an area in the image 302 covered by the least number of pixels that form a square or rectangle around a subject follicular unit 304 as shown in FIG. 3A wherein the axis aligned bounding are 316 forms a rectangle around the example 4-hair follicular unit 312. In an example, 1-FUA-c is computed as: the length of the diagonal 320, in pixels, multiplied by a maximum hair thickness 322 in pixels, which may be a constant chosen to represent the maximum thickness of hair (e.g. 1 or 2 pixels). The computation provides a measure or estimation of the maximum area covered by equivalent pixels of one hair follicle in the follicular unit under consideration.

Figure 3B:
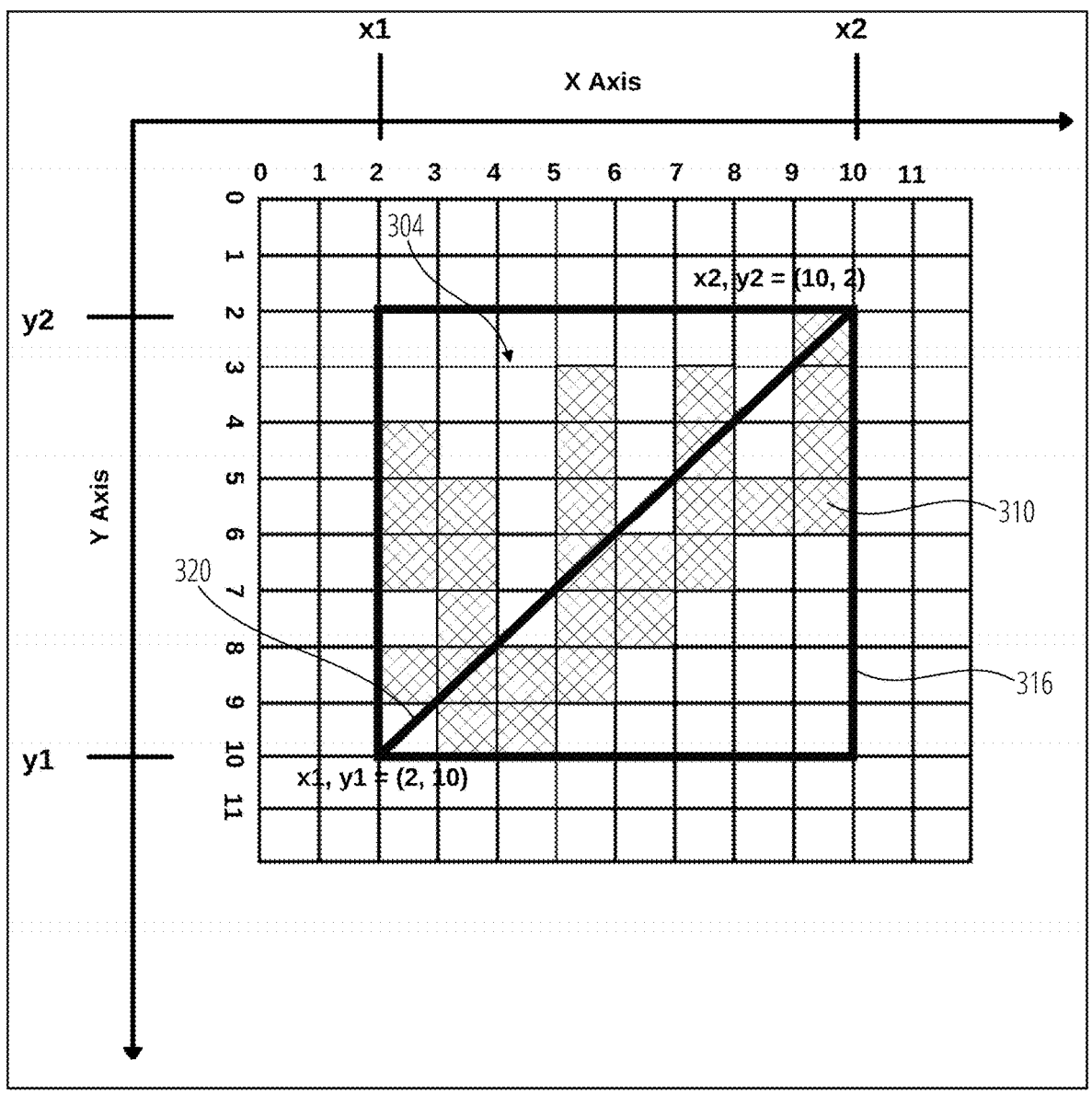
FIG. 3B depicts a sketch of another image in accordance with an illustrative embodiment.

In another illustrative embodiment, as shown in FIG. 3B, another image of another follicular unit 304 is shown to illustrate an example computation of 1-FUA-c and FUA-d.

width of 1 hair pixel (constant)=x, in the case of FIG. 3B 1 pixel

1 FUA-c=maximum diagonal length×width of 1 hair pixel (constant)

(maximum diagonal length)$^2$=(x2−x1)$^2$+(y2−y1)$^2$ (maximum diagonal length)$^2$=(10−2)$^2$+(10−2)$^2$ (maximum diagonal length)$^2$=(8)$^2$+(−8)$^2$ (maximum diagonal length)$^2$=128 maximum diagonal length=$\sqrt{128}$=11.31 pixels

FUA-d=count of all hair pixels in the folliculate unit under consideration

FUA-d=28 pixels

Further, a first ratio (R1) may be defined as (FUA-d)/(1-FUA-c) and a second ratio (R2) is defined as (BA-d)/(FUA-d). The parameters such (FUA-d), (1-FUA-c), (BA-d), (R1), and (R2) are referred to herein generally as area parameters of pixels. Any patient undergoing hair harvesting and implantation usually has a same thickness of hair in a given body surface, for example, the thickness of individual hair follicles on the scalp of a given patient is observed to remain largely the same. The physical length of the hair follicles also remains largely the same because of the use of a standard shaver/trimmer that establishes an even length of hair in a donor area (e.g. 2 mm). Through observations and heuristics of the area parameters of pixels related to an identified cluster, and the generally constant thickness of an individual's hair in a donor area, computations can be carried out to determine an appropriate classification for any determined cluster/graft in the cluster classification 408 of application 102.

In an example, it has been determined through repetitive computations and observations that for any follicular unit 304 of any patient, the computed absolute value of (FUA-d)−(1-FUA-c), if less than 5, is indicative of the follicular unit being a 1-hair-follicular unit 314. It has also been observed that the computed value of the first ratio (R1), if greater that about 2.13 (e.g. 2.13+/−0.01), is indicative of the subject follicular unit 304 in the image 302 being a 5- or more-hair-follicular unit. Further, the computed value of the first ratio (R1), if greater than about 1.85 and less than or equal to about 2.13, is indicative of the subject follicular unit 304 being a 4-hair follicular unit 312. Even further, the computed value of the first ratio (R1), if greater than or equal to about 1.6 and less than or equal to about 1.85, is indicative of the subject follicular unit 304 being a 3-hair follicular unit. Even further, it has been observed that a differentiation between 2 and 3-follicular units may be needed wherein a ratio of R2/R1 may be used. Herein R2/R1, if greater than about 1.98, is indicative of the subject follicular unit 304 being a 2-hair follicular unit whereas R2/R1 if greater than or equal to about 0.7 and less than or equal to about 1.98 is indicative of the subject follicular unit 304 being a 3 hair follicular unit. Table. 1 below shows a summary of example computation scenarios.

TABLE 1

Computation of follicular unit types

| Type | Computation |
|---|---|
| 5-Hair FU or more | R1 > 2.13 |
| 4-Hair FU | $R1 \geq 1.85$ and $R1 \leq 2.13$ or $R1 \geq 1.6$ and $R1 \leq 1.85$ and $\frac{R2}{R1} < 0.7$ |
| 3-Hair FU | $R1 \geq 1.6$ and $R1 \leq 1.85$ and $\frac{R2}{R1} \geq 0.7$ and $\frac{R2}{R1} \leq 1.98$ |
| 1-Hair FU | Abs([FUA − c] − [FUA − d] < 5) |

TABLE 1-continued

Computation of follicular unit types

| Type | Computation |
|---|---|
| 2-Hair FU | $R1 \geq 1.6$ and $R1 \leq 1.85$ and $\frac{R2}{R1} > 1.98$ |
| | or |
| | otherwise (none of the conditions are fulfilled) |

An example algorithm for categorizing the follicular units is shown below:

```
a) Given a graft, I , described by collection of pixels, a bounding box can
be computed as (Grafts[I].x2 − Grafts[I].x1) * (Grafts[I].y2 − Grafts[I].y1)
    b) maxRectangleArea = (Grafts[I].x2 − Grafts[I].x1) *
                 (Grafts[I].y2 − Grafts[I].y1)
            c) OneFUArea =
   sqrt(diagonal distance(Grafts[I].x1, Grafts[I].y1, Grafts[I].x2,
            Grafts[I].y2)) * OneHairPixelsInWidth
        d) ratio = total hair pixels in Grafts[I] / OneFUArea;
        e) ratioBB = maxRectangleArea / total hair pixels in Grafts[I];
        f) if (abs(OneFUArea − total hair pixels in Grafts[I]) < 5)
                    Grafts[I].noCount = 1U;
                else if (ratio > 2.13f) {
                    Grafts[I].noCount = 5U;
                    }
    else if (ratio > 1.85f && ratio <= 2.13f) { Grafts[I].noCount = 4U;}
        else if (ratio >= 1.6f && ratio <= 1.85f) //3FU
                { float rf = ratioBB / ratio;
                if(rf >= 0.7f && rf <= 1.98f)
                    {Grafts[I].noCount = 3U;}
                    else
                    if(rf > 1.98f)
                    {Grafts[I].noCount = 2U;}
                    else Grafts[I].noCount = 4U;
                    }
            else Grafts[I].noCount = 2U;
```

Of course, these examples are not meant to be limiting and other examples based on various combinations of parameters of the pixels that are related to a follicular unit 304 may be obtained in view of the specification. For example, cluster classification 408 may include determining a number of distinct hair follicles in the cluster by determining a bounding area 316 of the subject follicular unit 304/cluster and comparing the bounding area to a bounding area of 1-hair follicular units 314 obtained from analyzing a large number of images taken by a surgeon. For example, it may be determined from a large number (e.g. thousands) of images, taken during previous surgeries in which patients are shaved with a standard shaver that produces a defined remaining length of physical hair for harvesting and implantation, that a cluster representative of 1 follicle unit having 1 hair has a constant pixel width of "x". Cluster classification 408 of application 102 may thus determine that a computed bounding area 316 of "4x" is indicative of a cluster/graft/follicular unit 304 having 4 hair follicles, i.e. a 4-hair follicular unit 312, by virtue of it being 4 times larger than the area of 1-hair follicular units. This is achieved by taking into consideration a length of hair present during a harvesting and implantation procedure. Typically, the operator shaves a patient's scalp before operation by using a standard shaver that ensures that a defined length of hair is available for harvesting and implantation. Were the operator to use a non-standard shaver, cluster classification 408 may accept operator input about a patient specific length of hair in order to compensate for bounding area calculations. Generally, the larger the number of parameters used, the more accurate (correct classification in comparison to the ground truth) the cluster classification 408 is.

After cluster classification 408, the follicular unit analysis 420 may be completed by a replacement 410 step during which classified clusters or follicular units 304 are identified in the image 302 by replacing or masking pixels 306 belonging to the follicular unit 304 with defined colors, textures, shapes or otherwise visual cues that optimize or make it easier for an operator to recognize different follicular units 304 in real time even with patient and operator and camera 128 movements. The follicular unit analysis 420 is repeated for each new image obtained by the camera in order to provide a real time follicular unit analysis 420 for the patient. In an illustrative embodiment, the follicular unit analysis 420 is limited to a sub-section of a field of view of the camera 128 or maximum area of the images taken by the camera 128 such that as the camera 128 moves, only follicular units that fall within the subsection of the field of view/maximum are of the image are analyzed. In another example, the follicular unit analysis replaces or masks pixels 306 belonging to a pre-selected follicular unit type in the replacement 410 step. In yet another embodiment, based on knowledge of the coordinate system of the image and a coordinate system of a projector such as a laser projector, follicular units identified in the image 302 are visually highlighted by projecting a visual cue such as a defined light of the laser projector directly on the physical follicular unit of the patient's scalp.

Figure 6A:
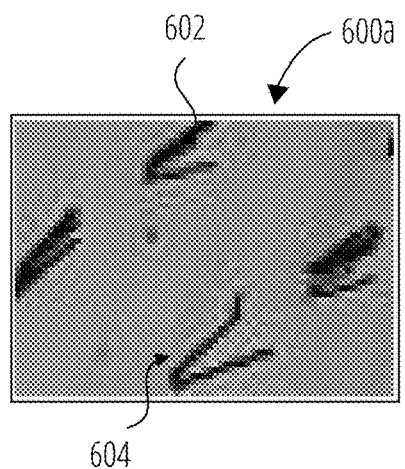
FIG. 6A depicts a sketch of an image in accordance with an illustrative embodiment.
Figure 6B:
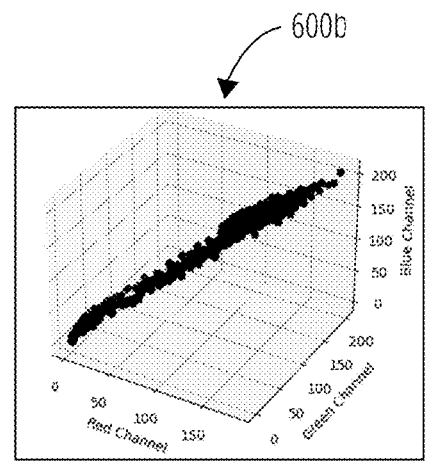
FIG. 6B depicts a chart in accordance with an illustrative embodiment.
Figure 6C:
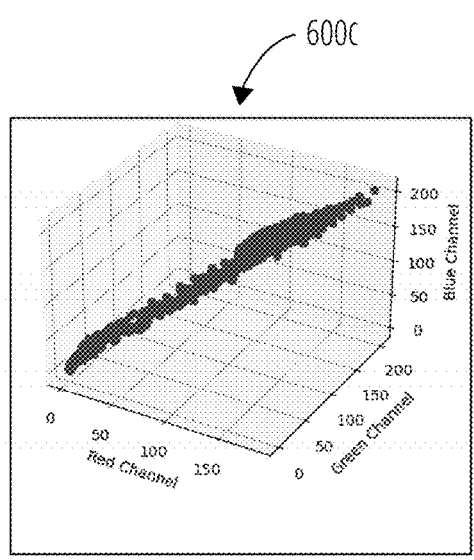
FIG. 6C depicts another chart in accordance with an illustrative embodiment.
Figure 6D:
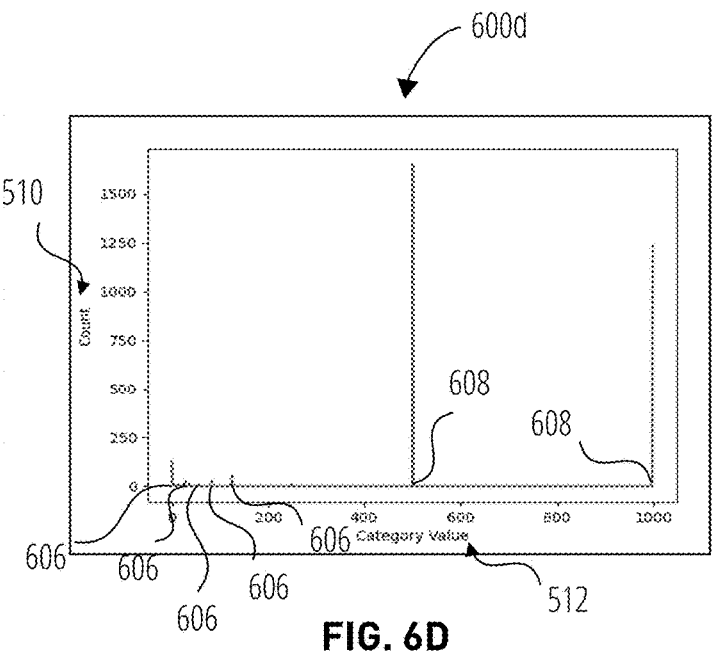
FIG. 6D depicts another chart in accordance with an illustrative embodiment.

Turning now to FIG. 6A-FIG. 6D, an example of an image 600a and corresponding hair pixel plot 600b, skin pixel plot 600c and histogram 600d for an example pixel type determination 404 step are shown. Image 600a is an image showing hair follicles 602 and grafts 604. By obtaining the r, g, b values of the hair pixels in image 600a and plotting them against each other, a hair pixel plot 600b is obtained. Similarly, a skin pixel plot 600c is obtained for skin pixels in image 600a. It can be seen that plotted values of the hair pixel plot 600b are generally similar to the plotted values of the skin pixel plot 600c as seen in FIG. 6B and FIG. 6C. Thus, finding a way to computationally segregate hair pixels of an individual from non-hair/skin pixels of the individual is beneficial. The histogram 600d of FIG. 6D achieves this differentiation through the determination of category values 512 and their count 510. The histogram 600d shows that hair category values 606, about 0-200, as shown in the figure, are on one side of the histogram 600d whereas skin category values 608, about 500 to 1000, are on another side of the histogram 600d.

Turning back to FIG. 4, the automated treatment planning 422 will now be discussed. The automated treatment planning 422 component of application 102 includes a donor area scanning 412 component, a grafts extraction calculation 414 component, a grafts extraction strategy and sequence 416 component and a handpiece tracking 418 component.

Figure 7A:
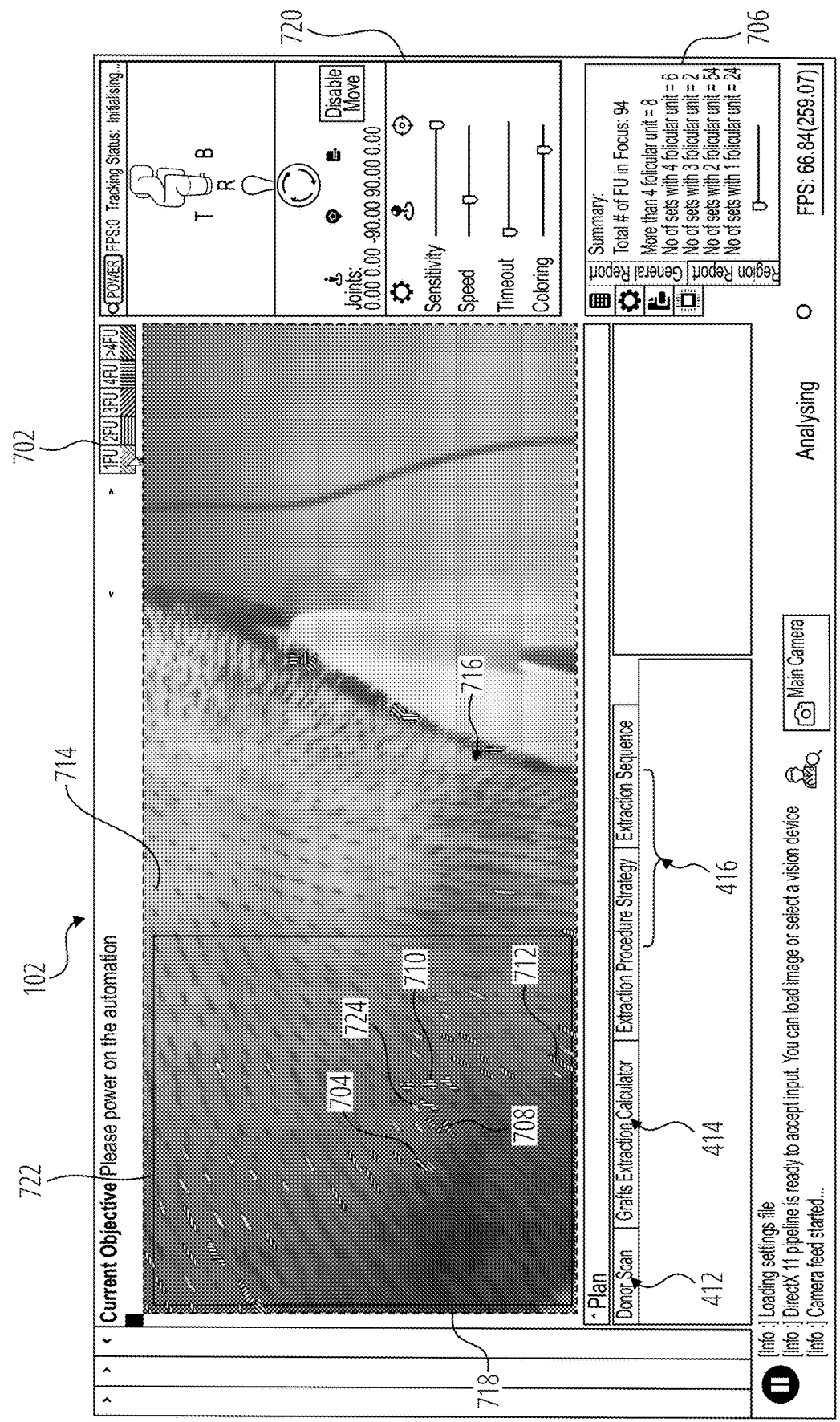
FIG. 7A depicts a sketch of an example application for optimized identification and classification of follicular units in accordance with an illustrative embodiment.
Figure 7B:
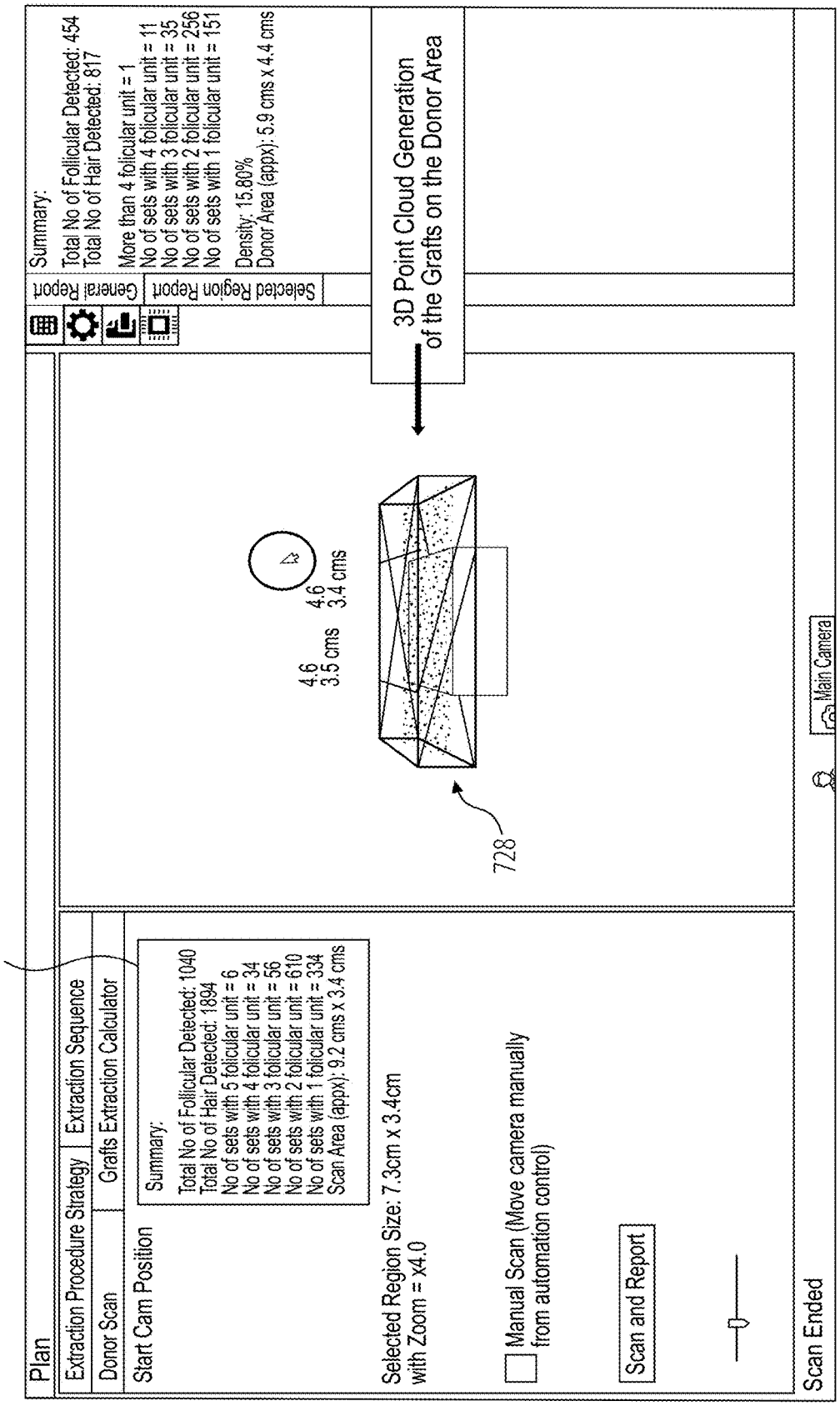
FIG. 7B depicts a sketch of an example application for static analysis in accordance with an illustrative embodiment.
Figure 7C:
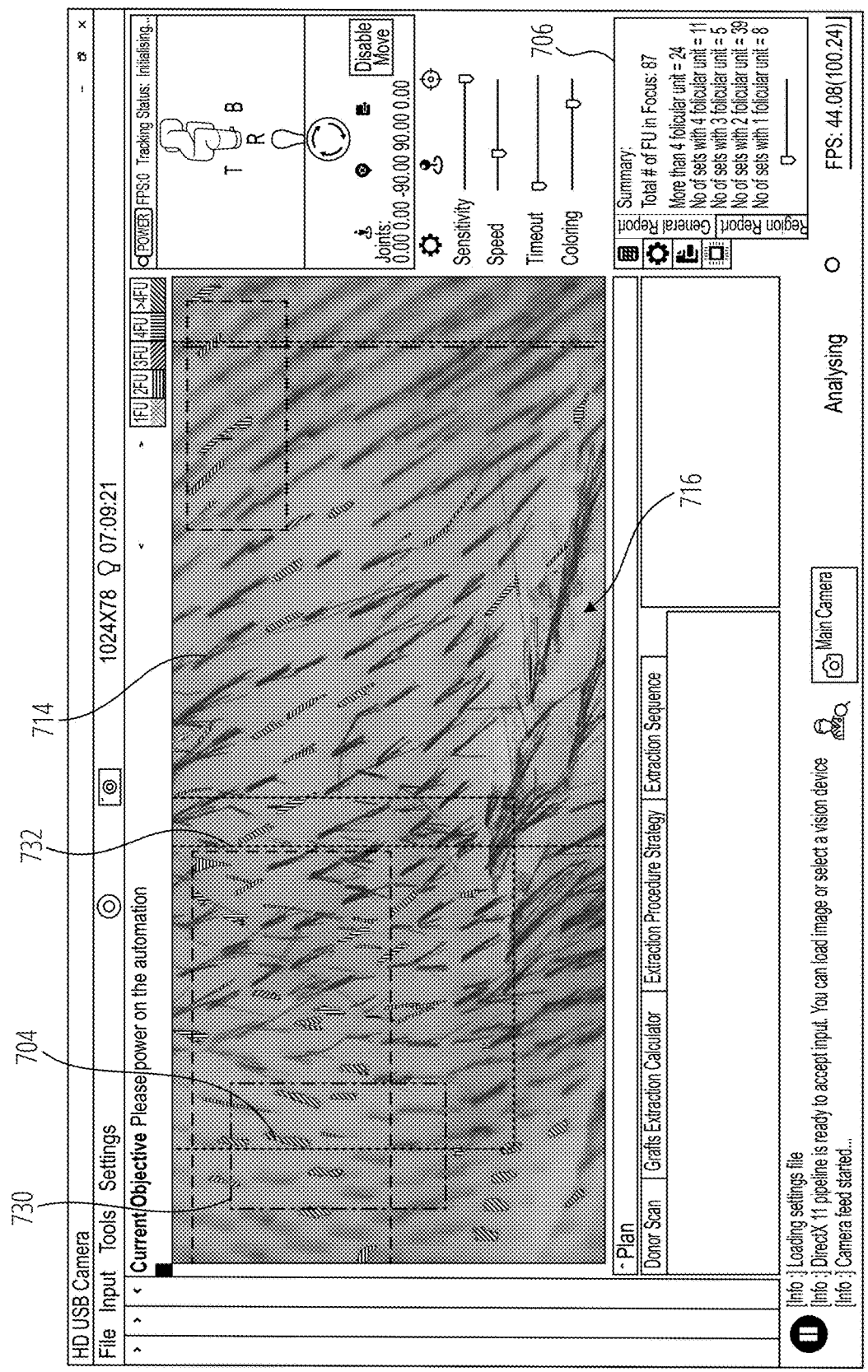
FIG. 7C depicts a zoomed in portion of the body surface in accordance with an illustrative embodiment.

Donor area scanning 412 includes scanning, using a camera or a 3D scanner, a donor area of a patient to produce a 3D point cloud or a 3D model of the surface. The 3D point cloud can also be converted into a mesh for modeling if needed. A digital format is the STL (Standard Tessellation Language) format. This format describes a succession of triangulated surfaces where each triangle is defined by three points and a normal surface. STL files may describe only the surface geometry of a three-dimensional object without any representation of color, texture or other CAD model attributes. However, other file formats have been developed to record color, transparency, or texture (such as Polygon File Format, PLY files). Irrespective of the type of imaging technology employed, a scanner projects light that is then reflected and recorded as individual images and compiled by an application after recognition of POI (points of interest). For example, two coordinates (x and y) of each point are evaluated on the image, and the third coordinate (z) is then calculated depending on a distance from the scanner. Further, 2D images taken by camera 128 can be registered together to form 3D images for the creation of a 3D model which is displayed by the donor area scanning 412 component. In an illustrative embodiment, as shown in FIG. 7A, the donor area scanning 412 begins with the operator providing a command, for example through application 102, to obtain a plurality of images 302 in a defined area of interest 722 of the patient's body surface/scalp. The defined area of interest 722 may be selected, for example, on a viewing area 718 of the application 102 using an input device of the harvesting system. The application 102 of FIG. 7A also shows a code such as a color code 702 representative of the different follicular units 304 and a dynamic report 706, such as a textual summary report, about properties of the detected follicular units on the body surface 716 as the camera moves. The colors of the color code are represented in FIG. 7A as different "textures" for illustration purposes. For example, the "1FU" color code may be a red color that indicates that follicular units being displayed with a red color are 1-hair follicular units 724. Different colors, shapes, textures or otherwise other visual cues may be chosen for each of the other follicular unit types in order to make them easily identifiable and distinguishable from each other. The dynamic report 706 changes based on analysis of the sequence of images obtained with movement of the camera. However, an operator may also select a defined area of interest 722 for static analysis. Upon selection of the defined area of interest 722 by the operator, the camera 128 traverses a physical space to obtain images such as 2D images or 3D single frame images of the scalp corresponding to the defined area of interest 722. The images are used to create a 3D point cloud 728 of follicular units (shown in FIG. 7B) with superimposed visual cues such as colors or shapes that are indicative of the types and locations of follicular units detected. A static report 726 of the defined area of interest 722 may be created based on follicular unit analysis of the defined area of interest using images corresponding to said area. Alternatively, to the 3D point cloud, a 3D model (not shown) such as a 3D color model of the imaged portion of the scalp may be created. The perspective of the 3D color model may be configured to be changeable by the operator in order to view different portions of the model and different hairs on the model. The operator may also zoom into and out of the 3D model for an optimized view. FIG. 7C shows a zoomed in portion of the body surface 716 wherein a first spotlight box 730 and a second spotlight box 730 are configured to draw attention to a type of follicular unit detected within the confined of the box. For example, the first spotlight box may draw attention to the presence of at least four>4-hair follicular units 704 in a defined area while the second spotlight box my draw attention to the presence of another type of number of follicular units in another area according to one or more predefined criteria. The position and/or sizes of one or more spotlight boxes may dynamically change as the camera moves in physical space to bring other parts of the body surface into view or focus. Further, the dynamic report 706 or count as per image feed is generated and shown. Further, a robotic arm controller 720 component may also be used to control the parameters of the robotic arm 126 and images taken by the camera 128 of the robotic arm 126, said parameters including, for example, a sensitivity of robotic arm 126 to commands, a speed of movement of the robotic arm 126, a timeout of the robotic arm 126 and a coloring of images 302 taken by the robotic arm.

Through a follicular unit analysis 420 of the defined area of interest 722, using individual images obtained or taken by the camera 128, properties of follicular units 304 in the defined area of interest 722 are obtained, said properties including a total number of follicular units 304 in the defined area of interest 722, different types and numbers of different types of follicular units 304 in the defined area of interest 722 and a location of the each identified follicular unit 304 in the defined area of interest 722. Said properties may be displayed on the 3D model for use by the operator.

The grafts extraction calculation 414 component provides for the operator, based on the results of the follicular unit analysis 420, the ability to determine a number of follicular units 304 to harvest, the types of follicular units 304 to harvest, and the location of follicular units 304 to harvest in order to maintain a desired appearance of a donor area, and a location of follicular units to implant in order to achieve a desired appearance of an implantation area. The determination utilizes one or more properties of the identified follicular units 304 and a set of rules about said properties such as one or more properties meeting a defined threshold, to perform steps of the grafts extraction calculation 414. For example, based on any combination of (i) a determined grade of baldness of the patient, (ii) a determined number of different types of follicular units 304 in a donor scan, (iii) a desired final look, such as density or shape of hair and (iv) a defined set of harvesting/implantation rules e.g. harvesting a maximum of 50% of available follicular units 304 in a donor area or implanting a minimum threshold number of hair follicles, the grafts extraction calculation 414 component determines a number and/or different types of follicular units to harvest from the donor area and a location of implantation in order to achieve the desired final look. The determination may be automated to guide an operator in a treatment planning and execution procedure. Further the grade of baldness may be provided as an input or may be automatically obtained from the images 302 based on detection of a threshold number of skin pixels in a unit area.

The grafts extraction strategy and sequence 416 component provides, based on the results of the follicular unit analysis 420, a strategy for harvesting/extracting follicular units 304 for hair 714 implantation. For example, follicular unit analysis 420 may determine that a defined area of interest 722 contains "x" number of 1-hair follicular units 724, "y" number of 2-hair follicular units 712, "m" number of 3-hair follicular units 708, "n" number of 4-hair follicular units 710 and "o" number of >4-hair follicular units 704. Grafts extraction strategy and sequence 416 components provides, for selection, a strategy for extracting the follicular units 304. The strategy is indicative of a plan of harvesting such as an "ascending plan", wherein follicular units 304 are extracted in the order of 1-hair follicular units 724, 2-hair follicular units 712, 3-hair follicular units 708 and so on. Thus, the robotic arm moves to all 1-hair follicular units 724 and the camera focusses on each 1-hair follicular units 724 earmarked for extraction before moving to 2-hair follicular units 712 earmarked for extraction. Similarly, another strategy, namely a "descending strategy" is used wherein the follicular units are extracted in a descending order of follicular unit types. In another strategy, the application 102 determines a set of sub-areas in the defined area of interest 722. A sequence of the sub-areas having the most number of follicular units starting from, for example, the sub-area having the largest number of follicular units 304 and ending at a sub-area having the lowest number of follicular units 304 are then determined and the robotic arm 126 with the camera 128 navigates sequentially to said areas for extraction.

The handpiece tracking 418 component detects a movement of the operator's handpiece on the patient's body surface 716, such as by employing image analyses of the images taken by the camera 128, and configures the robotic arm to follow the handpiece movements in order to automatically capture a live video of the body surface proximal to the operator's handpiece as harvesting and implantation proceeds.

Figure 8:
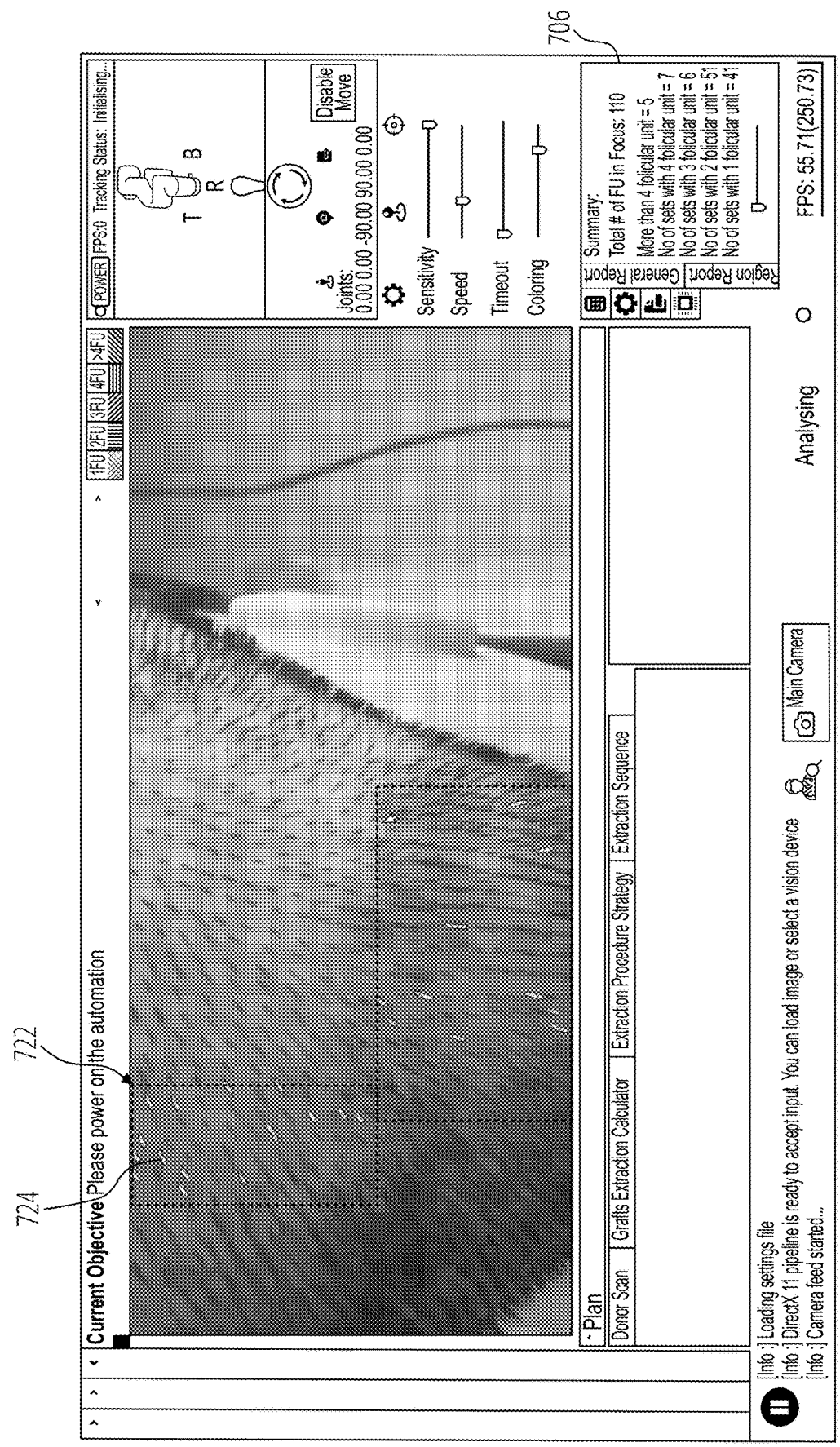
FIG. 8 depicts a sketch of an example application for optimized identification and classification of follicular units in accordance with an illustrative embodiment.

With reference to FIG. 8, the figure depicts the application 102 being configured to highlight follicular units 304 that are of a defined type, such as highlighting only 1-hair follicular units 724 in the defined area of interest 722 and ignoring other types of follicular units 304 in the defined area of interest 722. The dynamic report 706 may also be based on the highlighted 1-hair follicular units 724 or may incorporate information about ignored follicular unit types.

Figure 9:
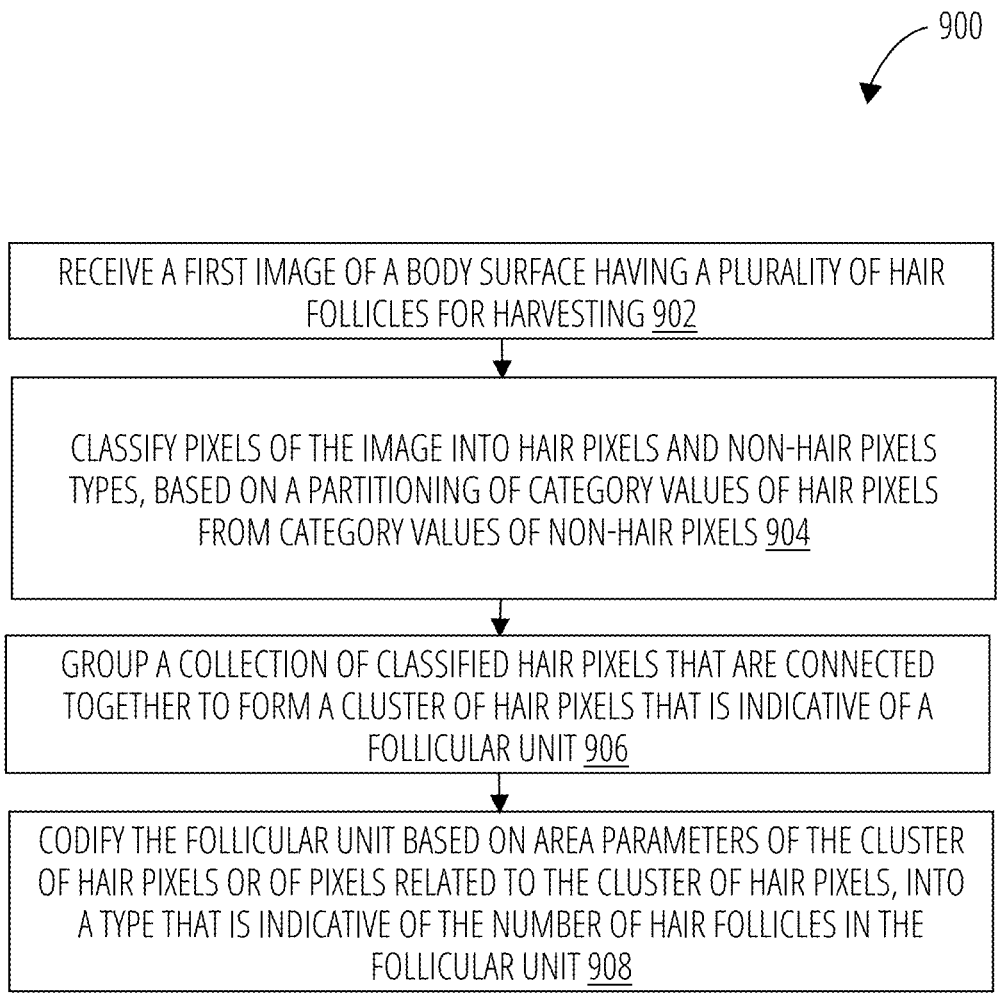
FIG. 9 depicts a flowchart of an example process in accordance with an illustrative embodiment.

FIG. 9 shows a process in which illustrative embodiments may be implemented. The process 900 begins at step 902, wherein the process 900 receives a first image of a body surface having a plurality of hair follicles for harvesting. In step 904, process 900 classifies pixels of the image into hair pixels and non-hair pixels types, based on a partitioning of category values of the hair pixels from category values of the non-hair pixels, the category values being representative of statistical properties of the hair and non-hair pixels. In step 906, process 900 groups, responsive to the classifying, a collection of proximal classified hair pixels together to form a cluster of hair pixels that is indicative of a follicular unit. In step 908, process 900 codifies the follicular unit, responsive to the grouping and based on area parameters of the cluster of hair pixels or area parameters of pixels related to the cluster of hair pixels, into a type that is indicative of the number of hair follicles in the follicular unit.

Figure 10:
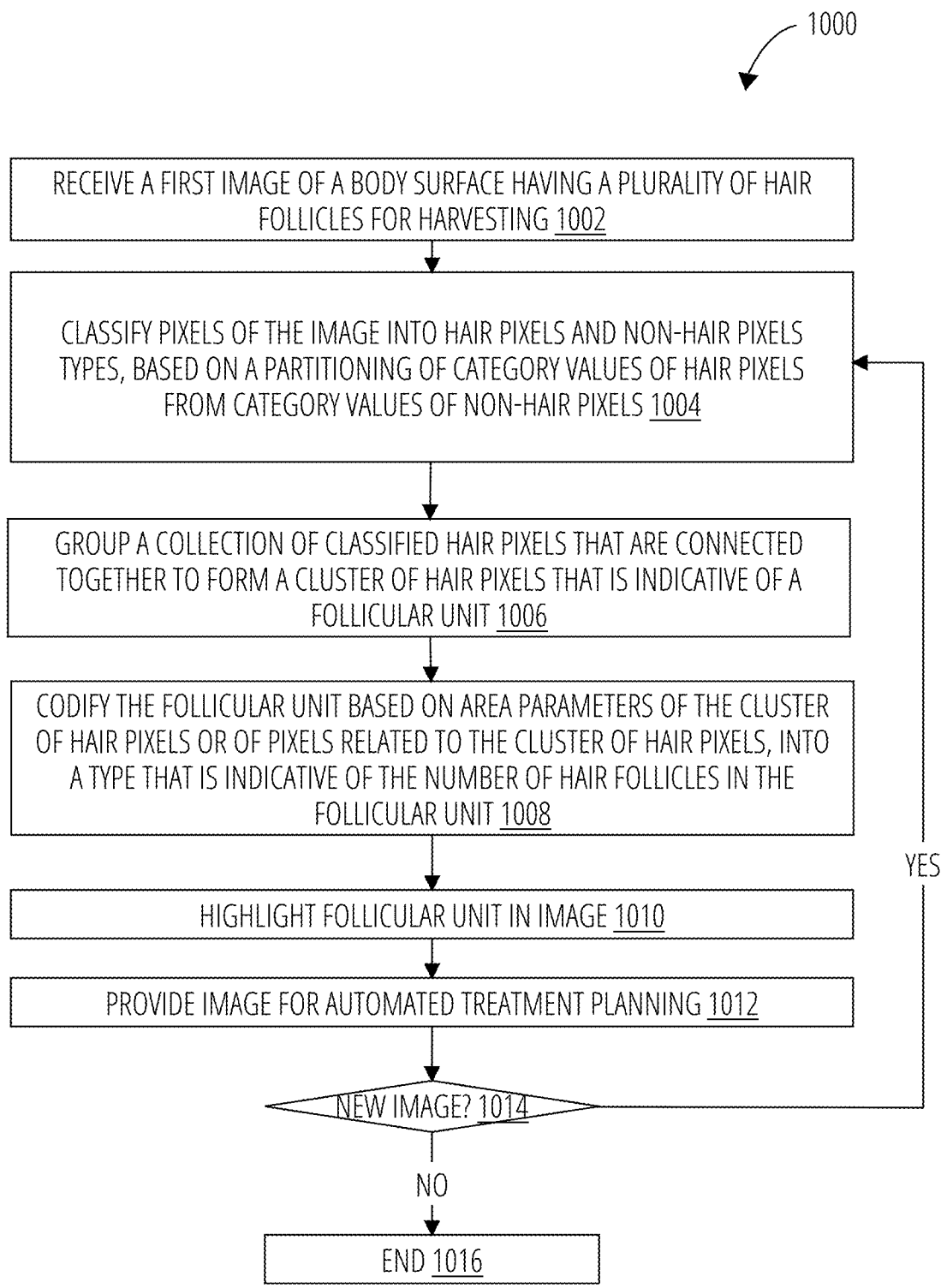
FIG. 10 depicts a flowchart of an example process in accordance with an illustrative embodiment.

FIG. 10 shows another process in which an illustrative embodiment is implemented. The process 1000 begins at step 1002, wherein the process 1000 receives a first image of a body surface having a plurality of hair follicles for harvesting. In step 1004, process 1000 classifies pixels of the image into hair pixels and non-hair pixels types, based on a partitioning of category values of the hair pixels from category values of the non-hair pixels, the category values being representative of statistical properties of the hair and non-hair pixels. In step 1006, process 1000 groups, responsive to the classifying, a collection of proximal classified hair pixels together to form a cluster of hair pixels that is indicative of a follicular unit. In step 1008, process 1000 codifies the follicular unit, responsive to the grouping and based on area parameters of the cluster of hair pixels or area parameters of pixels related to the cluster of hair pixels, into a type that is indicative of the number of hair follicles in the follicular unit. The follicular unit is highlighted in the image in step 1010 and the image is provided for automated treatment planning 422 in step 1012. Steps 1004-1012 are repeated for new images (step 1014) and the process 900 ends at step 1016.

Thus, a computer implemented method, system or apparatus, and computer program product are provided in the illustrative embodiments for hair harvesting and implantation and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser (e.g., web-based e-mail), or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, including but not limited to computer-readable storage devices as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method comprising the steps of:
   a) receiving a first image of a body surface having a plurality of hair follicles for harvesting;
   b) classifying pixels of the image into hair pixels and non-hair pixels types, based on a partitioning of category values of said hair pixels from category values of said non-hair pixels, the category values being representative of statistical properties of the hair and non-hair pixels;
   c) grouping, responsive to the classifying, a collection of proximal classified hair pixels together to form a cluster of hair pixels that is indicative of a follicular unit;
   d) categorizing the follicular unit, responsive to the grouping and based on area parameters of pixels related to the cluster of hair pixels, into a type that is indicative of the number of hair follicles in the follicular unit.

2. The method of claim 1, further comprising:
   receiving one or more other images in a live sequence and repeating steps a)-d) for the one or more other images.

3. The method of claim 2, further comprising:
   highlighting the categorized follicular unit by replacing pixels of said categorized follicular unit in the image with pixels indicative of one or more visual cues corresponding to the type that is categorized for the follicular unit.

4. The method of claim 3, wherein the one or more visual cues are visual cues selected from the group consisting of colors, numbers, shapes and textures.

5. The method of claim 2, -further comprising:
   projecting the live sequence on an augmented reality (AR) glasses or heads up display (HUD).

6. The method of claim 1, wherein the grouping is based on a flood fill algorithm.

7. The method of claim 1, wherein the area parameters include an area of the follicular unit, (FUA-d), a maximum area of a 1-hair follicular unit (1-FUA-c) in FUA-d, an axis aligned bounding area (BA-d), and ratios thereof.

8. The method of claim 1, wherein the classifying step is performed in a parallel manner and is achieved by:
   dividing the first image into sub-images, each sub-image comprising at least one pixel and classifying one of the sub images concurrently as at least another of the sub-images is classified, using a graphics processing unit (GPU) in order to increase a speed of classification in comparison to conventional serial classifications.

9. The method of claim 8, wherein the grouping is performed in a parallel manner using said sub-images and the GPU.

10. The method of claim 1, further comprising scanning an area of the body surface in order to obtain a 3D point cloud or 3D model of the body surface.

11. The method of claim 2, calculating a number and the type of follicular units to harvest form the body surface based on any combination of (i) a determined grade of baldness, (ii) a determined number of different types of follicular units on the body surface, (iii) a desired final look and (iv) a defined set of harvesting/implantation rules.

12. The method of claim 1, further comprising:
detecting a movement of an operator's handpiece on the body surface and moving a robotic arm having a camera to follow the movement in order to automatically capture a live video of the body surface proximal to the operator's handpiece.

13. The method of claim 3, further comprising displaying a textual report that includes information about the categorized follicular unit and updating the textual report based on the one or more other images.

14. A system comprising at least one processor configured to perform the steps comprising:
   a) receiving a first image of a body surface having a plurality of hair follicles for harvesting;
   b) classifying pixels of the image into hair pixels and non-hair pixels types, based on a partitioning of category values of said hair pixels from category values of said non-hair pixels, the category values being representative of statistical properties of the hair and non-hair pixels;
   c) grouping, responsive to the classifying, a collection of proximal classified hair pixels together to form a cluster of hair pixels that is indicative of a follicular unit;
   d) categorizing the follicular unit, responsive to the grouping and based on area parameters of pixels related to the cluster of hair pixels, into a type that is indicative of the number of hair follicles in the follicular unit.

15. The system of claim 14, wherein the processor is further configured to perform the steps of receiving one or more other images in a live sequence and repeating steps a)-d) for the one or more other images.

16. The system of claim 15, wherein the processor is further configured to perform the step of highlighting the categorized follicular unit by replacing pixels of said categorized follicular unit in the image with pixels indicative of one or more visual cues corresponding to the type that is categorized for the follicular unit.

17. The system of claim 16, wherein the one or more visual cues are visual cues selected from the group consisting of colors, numbers, shapes and textures.

18. The system of claim 15, wherein the processor is further configured to perform the steps of projecting the live sequence on an augmented reality (AR) glasses or heads up display (HUD).

19. A non-transitory computer-readable storage medium storing a program which, when executed by a processor, causes the processor to perform a procedure comprising:
   a) receiving a first image of a body surface having a plurality of hair follicles for harvesting;
   b) classifying pixels of the image into hair pixels and non-hair pixels types, based on a partitioning of category values of said hair pixels from category values of said non-hair pixels, the category values being representative of statistical properties of the hair and non-hair pixels;
   c) grouping, responsive to the classifying, a collection of proximal classified hair pixels together to form a cluster of hair pixels that is indicative of a follicular unit;
   d) categorizing the follicular unit, responsive to the grouping and based on area parameters of pixels related to the cluster of hair pixels, into a type that is indicative of the number of hair follicles in the follicular unit.

20. The non-transitory computer-readable storage medium of claim 19, wherein the processor further performs the steps of receiving one or more other images in a live sequence and repeating steps a)-d) for the one or more other images.

* * * * *